US008158557B2

(12) United States Patent
Schnabel et al.

(10) Patent No.: US 8,158,557 B2
(45) Date of Patent: Apr. 17, 2012

(54) STORAGE-STABLE FORMULATIONS OF SULFONAMIDES

(75) Inventors: Gerhard Schnabel, Elsenfeld (DE); Hans-Peter Krause, Hofheim (DE); Ralph Grohs, Düsseldorf (DE)

(73) Assignee: Bayer CropScience AG, Monheim (DE)

( * ) Notice: Subject to any disclaimer, the term of this patent is extended or adjusted under 35 U.S.C. 154(b) by 1502 days.

(21) Appl. No.: 11/517,458

(22) Filed: Sep. 8, 2006

(65) Prior Publication Data
US 2007/0054807 A1     Mar. 8, 2007

(30) Foreign Application Priority Data

Sep. 8, 2005 (EP) .................................... 05019531

(51) Int. Cl.
A01N 25/26 (2006.01)
A01N 43/64 (2006.01)
(52) U.S. Cl. ...................................... 504/100; 504/134
(58) Field of Classification Search .................. None
See application file for complete search history.

(56) References Cited

U.S. PATENT DOCUMENTS

| 5,057,144 | A | 10/1991 | Daum et al. |
| 5,534,486 | A | 7/1996 | Müller et al. |
| 6,054,410 | A | 4/2000 | Landes et al. |
| 6,559,098 | B1 | 5/2003 | Bratz et al. |
| 7,138,360 | B2 * | 11/2006 | Jager et al. ............... 504/211 |
| 2005/0009705 | A1 | 1/2005 | Feucht et al. |
| 2011/0190128 | A1 | 8/2011 | Ratschinski et al. |

FOREIGN PATENT DOCUMENTS

| EP | 0 007 687 A1 | 2/1980 |
| EP | 0 030 138 A1 | 6/1981 |
| EP | 0 764 404 A1 | 3/1997 |
| JP | 62084004 A | 4/1987 |
| WO | WO 97/10714 A1 | 3/1997 |
| WO | WO 98/34482 A1 | 8/1998 |
| WO | WO 03/026427 A1 | 4/2003 |

OTHER PUBLICATIONS

International Search Report for International Application No. PCT/EP2006/008447, European Patent Office, Netherlands, mailed on Nov. 13, 2006.
Dialog File 351, Accession No. 4046849, Derwent WPI English language abstract for JP 62084004 A, 1987.
Dialog FIle 351, Accession No. 8113908, Derwent WPI English language abstract for WO 97/10714 A1, 1997.
Dialog File 351, Accession No. 9072958, Derwent WPI English language abstract for WO 98/34482 A1, 1998.
Dialog File 351, Accession No. 13306343, Derwent WPI English language abstract for WO 03/026427 A1, 2003.

* cited by examiner

*Primary Examiner* — Alton Pryor
(74) *Attorney, Agent, or Firm* — Sterne, Kessler, Goldstein & Fox, P.L.L.C.

(57) ABSTRACT

The present invention relates to storage-stable solid water-dispersible formulations comprising one or more herbicidally active compounds from the group of the sulfonamides and their salts, one or more carrier materials and one or more wetting agents from the group of the naphthalenesulfonic acids and the group of the sulfosuccinic acid derivatives and also the salts of these groups.
The formulations according to the invention are suitable for use in crop protection.

18 Claims, No Drawings

STORAGE-STABLE FORMULATIONS OF SULFONAMIDES

The present invention relates to the field of crop protection compositions. In particular, the invention relates to storage-stable solid herbicide formulations which comprise herbicidally active compounds from the group of the sulfonamides and their salts, in particular phenylsulfonamides, such as phenylsulfonylaminocarbonyl-triazolinones or phenylsulfonylureas, heteroarylsulfonamides and other sulfonamides and their salts.

In general, active compounds for crop protection are not employed in pure form. Depending on the area of use and the type of use, and on physical, chemical and biological parameters, the active compound is used as an active compound formulation in a mixture with customary auxiliaries and additives. Also known are combinations with further active compounds for widening the activity spectrum and/or for protecting crop plants (for example by safeners, antidotes).

In general, formulations of active compounds for crop protection should have high chemical and physical stability, should be easy to apply and easy to use and have broad biological action combined with high selectivity.

Solid formulations of active compounds from the group of the sulfonylureas are known per se, for example from WO-A-97/10714.

In general, herbicidally active compounds from the group of the sulfonamides have high chemical reactivity and tend to undergo chemical degradation, for example by hydrolysis. With respect to a sufficient storage stability of the formulations, this has to be judged critical, and the particular storage temperatures to be expected in the intended markets also have to be taken into account.

A stabilization of sulfonylureas comprised in solid formulations is described, for example, in JP-A-62-084004, where calcium carbonate and Na tripolyphosphate are added as stabilizers. However, in addition the formulations for their part, owing to the auxiliaries and additives comprised therein, may also affect the stability of the active compounds.

WO-A-98/34482 describes results of tests with the phenylsulfonylureas tritosulfuron and metsulfuron according to which additives (adjuvants) from the group of the fatty alcohol ethoxylates and the ethoxylated fatty amines result in lower storage stability than adjuvants from the group of the sodium salts of the aliphatic sulfonic acids, such as Na alkanesulfonates and Na alpha-olefinsulfonates. EP-A-764404 describes a stabilization of the heteroarylsulfonylurea flazasulfuron using Na dioctylsulfosuccinate.

However, corresponding stability studies with active compounds from the group of the phenylsulfonylaminocarbonyltriazolinones alone and in mixtures with other active compounds from the group of the sulfonamides are not known. In the applicant's tests, it was found that in particular wetting agents, such as anionic wetting agents from the group of the alkyl sulfates and alkyl sulfonates and also nonionic wetting agents from the group of the alkyl alkoxylates, which are routinely used in formulations of crop protection agents, may result in an instability of active compounds from the group of the sulfonamides.

It was an object of the present invention to provide an improved solid formulation of crop protection agents, which permits a high storage stability of active compounds from the group of the sulfonamides and, in addition, has unchanged high biological effectiveness and crop plant compatibility.

This object is achieved by the solid water-dispersible formulation according to the present invention.

Accordingly, the present invention relates to a solid water-dispersible formulation comprising:
(a) one or more active compounds from the group of the sulfonamides and their salts, with at least one active compound from the group of the phenylsulfonylaminocarbonyltriazolinones,
(b) one or more carrier materials,
where
(c) one or more wetting agents from the group of the naphthalenesulfonic acids and the group of the sulfosuccinic acid derivatives and the salts of these groups are used.

In addition, the solid water-dispersible formulation according to the invention may, as further components, optionally also comprise:
(d) further customary auxiliaries and additives,
(e) one or more safeners, and
  (e-1) solvents,
  (e-2) emulsifiers and
  (e-3) carrier materials required, if appropriate, for the safener addition,
(f) one or more agrochemically active compounds different from (a) and (e).

A preferred embodiment of the present invention consists in the use of at least two or more active compounds from the group of the sulfonamides and their salts (component a), preferably with active compounds from the group of the phenylsulfonamides, such as phenylsulfonylaminocarbonyltriazolinones or phenylsulfonylureas.

A further preferred embodiment of the present invention consists in the use of at least two or more active compounds from the group of the sulfonamides and their salts (component a), preferably with active compounds from the group of the phenylsulfonamides, such as phenylsulfonylaminocarbonyltriazolinones or phenylsulfonylureas, and of one or more safeners (component e) and the solvents (component e-1), emulsifiers (component e-2) and carrier materials (component e-3) required, if appropriate, for the safener addition.

Preferred sulfonamides (component a) are phenylsulfonamides, such as phenylsulfonylaminocarbonyltriazolinones or phenylsulfonylureas, heteroarylsulfonamides and other sulfonamides, such as amidosulfuron, and their salts. Preferred phenylsulfonamides are compounds from the group of the phenylsulfonylaminocarbonyltriazolinones or the phenylsulfonylureas. The term "phenylsulfonylurea" is to be understood as including those sulfonylureas in which the phenyl group is attached via a spacer such as $CH_2$, O or NH to the sulfone group ($SO_2$). Examples of phenylsulfonylaminocarbonyltriazolinones are flucarbazone, propoxycarbazone or methyl 4-[(4,5-dihydro-3-methoxy-4-methyl-5-oxo-1H-1,2,4-triazol-1-yl)carboxamidosulfonyl]-5-metylthiophene-3-carboxylate (known, for example, from WO-A-03/026427, example 1-2) and/or their salts. The sulfonamides are commercially available and/or can be prepared by known processes, as described, for example, in EP-A-7687, EP-A-30138, U.S. Pat. No. 5,057,144 and U.S. Pat. No. 5,534,486.

Suitable phenylsulfonamides are, for example, phenylsulfonamides of the formula (I) and/or salts thereof

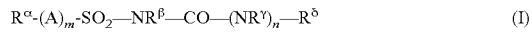

$$R^\alpha\text{-}(A)_m\text{-}SO_2\text{—}NR^\beta\text{—}CO\text{—}(NR^\gamma)_n\text{—}R^\delta \qquad (I)$$

in which
$R^\alpha$ is an unsubstituted or substituted phenyl radical, where the phenyl radical including substituents has 1-30 carbon atoms, preferably 1-20 carbon atoms,
$R^\ominus$ is a hydrogen atom or an unsubstituted or substituted hydrocarbon radical which, including substituents, has 1-10 carbon atoms, for example unsubstituted or substituted $C_1$-$C_6$-alkyl, preferably a hydrogen atom or methyl, $R^\gamma$ is a hydrogen atom or an unsubstituted or substituted hydrocarbon radical which, including substituents, has 1-10 carbon atoms, for example unsubstituted or substituted $C_1$-$C_6$-alkyl, preferably a hydrogen atom or methyl, A is $CH_2$, O or NH, preferably O, m is zero or 1, n is zero or 1, preferably 1, and $R^\delta$ is a heterocyclic radical, such as a pyrimidinyl radical, a triazinyl radical or a triazolinone radical.

Preferred phenylsulfonamides are phenylsulfonylureas, for example phenylsulfonylureas of the formula (II) and/or salts thereof

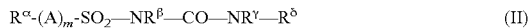

in which $R^\alpha$ is an unsubstituted or substituted phenyl radical, where the phenyl radical including substituents has 1-30 carbon atoms, preferably 1-20 carbon atoms, $R^\beta$ is a hydrogen atom or an unsubstituted or substituted hydrocarbon radical which, including substituents, has 1-10 carbon atoms, for example unsubstituted or substituted $C_1$-$C_6$-alkyl, preferably a hydrogen atom or methyl, $R^\beta$ is a hydrogen atom or an unsubstituted or substituted hydrocarbon radical which, including substituents, has 1-10 carbon atoms, for example unsubstituted or substituted $C_1$-$C_6$-alkyl, preferably a hydrogen atom or methyl, A is $CH_2$, O or NH, preferably O, m is zero or 1, and $R^\delta$ is a heterocyclic radical, such as a pyrimidinyl radical or a triazinyl radical.

Preference is given to phenylsulfonylureas of the formula (III) and/or salts thereof

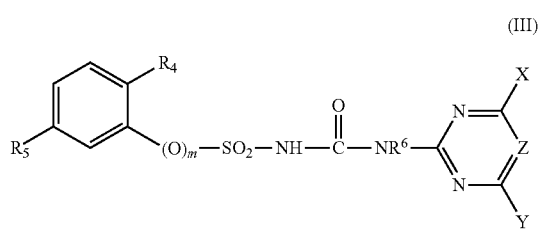

in which $R^4$ is $C_1$-$C_4$-alkoxy, preferably $C_2$-$C_4$-alkoxy, or CO-$R^a$, where $R^a$ is OH, $C_1$-$C_4$-alkoxy or $NR^bR^c$, where $R^b$ and $R^c$ are identical or different and independently of one another are H or $C_1$-$C_4$-alkyl, $R^5$ is halogen, preferably iodine, or (A)$_n$-$NR^dR^e$, where n is zero or 1, A is a group CR'R", where R' and R" are identical or different and independently of one another are H or $C_1$-$C_4$-alkyl, $R^d$ is H or $C_1$-$C_4$-alkyl and $R^e$ is an acyl radical, such as formyl, or $C_1$-$C_4$-alkylsulfonyl, and if $R^4$ is $C_1$-$C_4$-alkoxy, preferably $C_2$-$C_4$-alkoxy, $R^5$ may also be H, $R^6$ is H or $C_1$-$C_4$-alkyl, m is zero or 1, X and Y are identical or different and independently of one another are halogen or NR'R", where R' and R" are identical or different and are H or $C_1$-$C_4$-alkyl, or $C_1$-$C_6$-alkyl, $C_1$-$C_6$-alkoxy, $C_1$-$C_6$-alkylthio, $C_3$-$C_6$-cycloalkyl, $C_2$-$C_6$-alkenyl, $C_2$-$C_6$-alkynyl, $C_3$-$C_6$-alkenyloxy or $C_3$-$C_6$-alkynyloxy, where each of the eight lastmentioned radicals is unsubstituted or substituted by one or more radicals from the group consisting of halogen, $C_1$-$C_4$-alkoxy and $C_1$-$C_4$-alkylthio, preferably $C_1$-$C_4$-alkyl or $C_1$-$C_4$-alkoxy, and Z is CH or N.

Particular preference is given to phenylsulfonylureas of the formula (III) and/or salts thereof, in which a) $R^4$ is CO—($C_1$-$C_4$-alkoxy), $R^5$ is halogen, preferably iodine, or $R^5$ is $CH_2$—$NHR^e$, where $R^e$ is an acyl radical, preferably $C_1$-$C_4$-alkylsulfonyl, and m is zero, b) $R^4$ is CO—N($C_1$-$C_4$-alkyl)$_2$, $R^5$ is $NHR^e$, where $R^e$ is an acyl radical, preferably formyl, and m is zero, or c) $R^4$ is $C_2$-$C_4$-alkoxy, $R^5$ is H and m is 1.

Typical phenylsulfonylureas are, inter alia, the compounds listed below and their salts, such as the sodium salts: bensulfuron-methyl, chlorimuron-ethyl, chlorsulfuron, cinosulfuron, cyclosulfamuron, ethametsulfuron-methyl, ethoxysulfuron and its sodium salt, metsulfuron-methyl, oxasulfuron, primisulfuron-methyl, prosulfuron, sulfometuron-methyl, triasulfuron, tribenuron-methyl, triflusulfuron-methyl, tritosulfuron, iodosulfuron-methyl and its sodium salt (WO-A-92/13845), mesosulfuron-methyl and its sodium salt (Agrow No. 347, Mar. 3, 2000, page 22 (PJB Publications Ltd. 2000)) and foramsulfuron and its sodium salt (Agrow No. 338, Oct. 15, 1999, page 26 (PJB Publications Ltd. 1999)).

Particularly preferred phenylsulfonamides are: iodosulfuron-methyl and its sodium salt, mesosulfuron-methyl and its sodium salt, foramsulfuron and its sodium salt, flucarbazone and its sodium salt, propoxycarbazone and its sodium salt, methyl 4-[(4,5-dihydro-3-methoxy4-methyl-5-oxo-1H-1,2,4-triazol-1-yl)carboxamidosulfonyl]-5-metylthiophene-3-carboxylate and its sodium salt, and ethoxysulfuron and its sodium salt, metsulfuron-methyl and its sodium salt, tribenuron-methyl and its sodium salt, chlorsulfuron and its sodium salt.

The active compounds listed above are known, for example, from "The Pesticide Manual", 12th edition, The British Crop Protection Council (2000), or the literature references given after the individual active compounds.

Suitable heteroarylsulfonamides are, for example, compounds from the group of the heteroarylsulfonylaminocarbonyltriazolinones or the heteroarylsulfonylureas, preferably from the group of the heteroarylsulfonylureas. The term "heteroarylsulfonylureas" is to be understood as including those sulfonylureas in which the heteroaryl group is attached via a spacer such as $CH_2$, O or NH to the sulfone group ($SO_2$).

Suitable heteroarylsulfonamides are, for example, sulfonamides of the formula (IV) and/or salts thereof,

in which $R^{\alpha'}$ is an unsubstituted or substituted heteroaryl radical, where the heteroaryl radical including substituents has 1-30 carbon atoms, preferably 1-20 carbon atoms, $R^{\beta'}$ is a hydrogen atom or an unsubstituted or substituted hydrocarbon radical which, including substituents, has 1-10 carbon atoms, for example unsubstituted or substituted $C_1$-$C_6$-alkyl, preferably a hydrogen atom or methyl, $R^{\gamma'}$ is a hydrogen atom or an unsubstituted or substituted hydrocarbon radical which, including substituents, has 1-10 carbon atoms, for example unsubstituted or substituted $C_1$-$C_6$-alkyl, preferably a hydrogen atom or methyl, A' is $CH_2$, O or NH, preferably O, m' is zero or 1, n' is zero or 1, preferably 1, and $R^{\delta'}$ is a heterocyclic radical, such as a pyrimidinyl radical, a triazinyl radical or a triazolinone radical.

Preferred heteroarylsulfonamides are heteroarylsulfonylureas, for example sulfonylureas of the formula (V) and/or salts thereof,

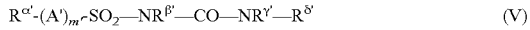

in which

R^α is an unsubstituted or substituted heteroaryl radical, where the heteroaryl radical including substituents has 1-30 carbon atoms, preferably 1-20 carbon atoms, R^β' is a hydrogen atom or an unsubstituted or substituted hydrocarbon radical which, including substituents, has 1-10 carbon atoms, for example unsubstituted or substituted $C_1$-$C_6$-alkyl, preferably a hydrogen atom or methyl, R^γ' is a hydrogen atom or an unsubstituted or substituted hydrocarbon radical which, including substituents, has 1-10 carbon atoms, for example unsubstituted or substituted $C_1$-$C_6$-alkyl, preferably a hydrogen atom or methyl, A' is $CH_2$, O or NH, preferably O, m' is zero or 1, and R^δ' is a heterocyclic radical, such as a pyrimidinyl radical or a triazinyl radical.

Particular preference is given to heteroarylsulfonamides of the formula (VI) below $$R^{α'}\text{-}SO_2\text{-}NH\text{-}CO\text{-}(NR^{γ'})_n\text{-}R^{δ'} \quad (VI)$$

in which

R^α' is a substituted heteroaryl radical such as substituted pyridyl, thienyl, pyrazolyl or imidazolyl, R^γ' is H, ($C_1$-$C_3$)-alkyl, unsubstituted or substituted by halogen (F, C, Br, I) or halo-($C_1$-$C_3$)-alkoxy, preferably H or methyl, for n'=1, R^δ' is a pyrimidinyl radical or a triazinyl radical, preferably and for n'=zero, R^δ' is a triazolinone radical, preferably $R^7$ is ($C_1$-$C_{10}$)-alkyl, which is unsubstituted or substituted by halogen (F, Cl, Br, I) or halo-($C_1$-$C_3$)-alkyl, $R^8$ is ($C_1$-$C_{10}$)-alkyl, which is unsubstituted or substituted by halogen (F, Cl, Br, I) or halo-($C_1$-$C_3$)-alkyl, X and Y are identical or different and independently of one another are halogen or NR'R", where R' and R" are identical or different and are H or $C_1$-$C_4$-alkyl, or $C_1$-$C_6$-alkyl, $C_1$-$C_6$-alkoxy, $C_1$-$C_6$-alkylthio, $C_3$-$C_6$-cycloalkyl, $C_2$-$C_6$-alkenyl, $C_2$-$C_6$-alkynyl, $C_3$-$C_6$-alkenyloxy or $C_3$-$C_6$-alkynyloxy, where each of the eight lastmentioned radicals is unsubstituted or substituted by one or more radicals from the group consisting of halogen, $C_1$-$C_4$-alkoxy and $C_1$-$C_4$-alkylthio, preferably $C_1$-$C_4$-alkyl or $C_1$-$C_4$-alkoxy.

Particularly preferably, R^α' is in which $R^9$ is ($C_1$-$C_6$)-alkyl, ($C_1$-$C_6$)-alkoxy, ($C_2$-$C_6$)-alkenyloxy, ($C_2$-$C_6$)-alkynyloxy, ($C_1$-$C_6$)-alkylsulfonyl, ($C_1$-$C_6$)-alkylcarbonyl, ($C_1$-$C_6$)-alkoxycarbonyl, ($C_2$-$C_6$)-alkenyloxycarbonyl, ($C_2$-$C_6$)-alkynyloxycarbonyl, CONR'R", halo-($C_1$-$C_6$)-alkyl, halo-($C_1$-$C_6$)-alkoxy, halo-($C_2$-$C_6$)-alkenyloxy, halo-($C_2$-$C_6$)-alkynyloxy, halo-($C_1$-$C_6$)-alkylsulfonyl, halo-($C_1$-$C_6$)-alkyl-carbonyl, halo-($C_1$-$C_6$)-alkoxycarbonyl, halo-($C_2$-$C_6$)-alkenyloxycarbonyl, halo-($C_2$-$C_6$)-alkynyloxycarbonyl, $R^{10}$ is H, ($C_1$-$C_3$)-alkyl, ($C_1$-$C_3$)-alkoxy, halo-($C_1$-$C_3$)-alkyl, halo-($C_1$-$C_3$)-alkoxy or halogen (F, Cl, Br, I), l is zero or 1, $R^{11}$ is ($C_1$-$C_6$)-alkyl, ($C_1$-$C_6$)-alkoxy, ($C_2$-$C_6$)-alkenyloxy, ($C_2$-$C_6$)-alkynyloxy, ($C_1$-$C_6$)-alkylsulfonyl, ($C_1$-$C_6$)-alkylcarbonyl, ($C_1$-$C_6$)-alkoxycarbonyl, ($C_2$-$C_6$)-alkenyloxycarbonyl, ($C_2$-$C_6$)-alkynyloxycarbonyl, halo-($C_1$-$C_6$)-alkyl, halo-($C_1$-$C_6$)-alkoxy, halo-($C_2$-$C_6$)-alkenyloxy, halo-($C_2$-$C_6$)-alkynyloxy, halo-($C_1$-$C_6$)-alkylsulfonyl, halo-($C_1$-$C_6$)-alkyl-carbonyl, halo-($C_1$-$C_6$)-alkoxycarbonyl, halo-($C_2$-$C_6$)-alkenyloxycarbonyl, halo-($C_2$-$C_6$)-alkynyloxycarbonyl, CONR'R", $R^{12}$ is halogen (F, Cl, Br, I), ($C_1$-$C_6$)-alkyl, ($C_1$-$C_6$)-alkoxy, ($C_1$-$C_6$)-alkylsulfonyl, ($C_1$-$C_6$)-alkoxycarbonyl, ($C_2$-$C_6$)-alkenyloxycarbonyl, ($C_2$-$C_6$)-alkynyloxy-carbonyl, halo-($C_1$-$C_6$)-alkyl, halo-($C_1$-$C_6$)-alkoxy, halo-($C_1$-$C_6$)-alkylsulfonyl, halo-($C_1$-$C_6$)-alkoxycarbonyl, halo-($C_2$-$C_6$)-alkenyloxycarbonyl, halo-($C_2$-$C_6$)-alkynyloxycarbonyl, $R^{13}$ is ($C_1$-$C_6$)-alkoxycarbonyl, ($C_2$-$C_6$)-alkenyloxycarbonyl, ($C_2$-$C_6$)-alkynyl-oxycarbonyl, ($C_1$-$C_6$)-alkyl, ($C_1$-$C_6$)-alkoxy, ($C_1$-$C_6$)-alkylsulfonyl, halo-($C_1$-$C_6$)-alkoxycarbonyl, halo-($C_2$-$C_6$)-alkenyloxycarbonyl, halo-($C_2$-$C_6$)-alkynyloxycarbonyl, halo-($C_1$-$C_6$)-alkyl, halo-($C_1$-$C_6$)-alkoxy, halo-($C_1$-$C_6$)-alkylsulfonyl, halogen (F, Cl, Br, I), CONR'R", or $R^{13}$ is a heterocyclic ring, which may be saturated, unsaturated or aromatic and which preferably contains 4-6 ring atoms and one or more heteroatoms from the group consisting of N, O and S and which may be unsubstituted or substituted by one or more substituents, preferably from the group consisting of ($C_1$-$C_3$)-alkyl, ($C_1$-$C_3$)-alkoxy, halo-($C_1$-$C_3$)-alkyl, halo-($C_1$-$C_3$)-alkoxy and halogen, particularly preferably $R^{14}$ is H, halogen (F, C, Br, I), ($C_1$-$C_6$)-alkyl, halo-($C_1$-$C_6$)-alkyl, $R^{15}$ is H, $(C_1-C_6)$-alkyl, halo-$(C_1-C_6)$-alkyl, $R^{16}$ is $(C_1-C_6)$-alkyl, $(C_1-C_6)$-alkoxy, $(C_2-C_6)$-alkenyloxy, $(C_2-C_6)$-alkynyloxy, $(C_1-C_6)$-alkylsulfonyl, $(C_1-C_6)$-alkylcarbonyl, $(C_1-C_6)$-alkoxycarbonyl, $(C_2-C_6)$-alkenyloxycarbonyl, $(C_2-C_6)$-alkynyloxycarbonyl, halo-$(C_1-C_6)$-alkyl, halo-$(C_1-C_6)$-alkoxy, halo-$(C_2-C_6)$-alkenyloxy, halo-$(C_2-C_6)$-alkynyloxy, halo-$(C_1-C_6)$-alkylsulfonyl, halo-$(C_1-C_6)$-alkylcarbonyl, halo-$(C_1-C_6)$-alkoxycarbonyl, halo-$(C_2-C_6)$-alkenyloxycarbonyl, halo-$(C_2-C_6)$-alkynyloxycarbonyl, CONR'R", in particular $SO_2$-ethyl, and R' and R" independently of one another are H, $(C_1-C_6)$-alkyl, halo-$(C_1-C_6)$-alkyl, $(C_2-C_6)$-alkenyl, $(C_2-C_6)$-haloalkenyl, $(C_2-C_6)$-alkynyl, $(C_2-C_6)$-haloalkynyl, or NR'R" forms a heterocyclic ring which may be saturated, unsaturated or aromatic and which preferably contains 4-6 ring atoms and one or more heteroatoms from the group consisting of N, O and S and which may be unsubstituted or substituted by one or more substituents, preferably from the group consisting of $(C_1-C_3)$-alkyl, $(C_1-C_3)$-alkoxy, halo-$(C_1-C_3)$-alkyl, halo-$(C_1-C_3)$-alkoxy and halogen.

Particularly preferred heteroarylsulfonylureas are, for example, nicosulfuron and its salts, such as the sodium salt, rimsulfuron and its salts, such as the sodium salt, thifensulfuron-methyl and its salts, such as the sodium salt, pyrazosulfuron-ethyl and its salts, such as the sodium salt, flupyrsulfuron-methyl and its salts, such as the sodium salt, sulfosulfuron and its salts, such as the sodium salt, trifloxysulfuron and its salts, such as the sodium salt, azimsulfuron and its salts, such as the sodium salt, flazasulfuron and its salts, such as the sodium salt, and flucetosulfuron (1-[3-[[[[(4,6-dimethoxy-2-pyrimidinyl)amino]carbonyl]amino]sulfonyl]-2-pyridinyl]-2-fluoropropyl methoxyacetate) and its salts, such as the sodium salt.

The active compounds listed above are known, for example, from "The Pesticide Manual", 12th edition, The British Crop Protection Council (2000), or the literature references given after the individual active compounds.

For the purpose of the present invention, the sulfonamides (component a) contained in the solid, water-dispersible formulations according to the invention are in each case to be understood as meaning all use forms, such as acids, esters, salts and isomers, such as stereoisomers and optical isomers. Thus, in addition to neutral compounds, their salts with inorganic and/or organic counterions are in each case meant to be included. Thus, sulfonamides are capable of forming salts, for example, in which the hydrogen of the —$SO_2$—NH group is replaced by an agriculturally suitable cation. These salts are, for example, metal salts, in particular alkali metal salts or alkaline earth metal salts, in particular sodium and potassium salts, or else ammonium salts or salts with organic amines. Salt formation may also take place by addition of an acid to basic groups, such as, for example, amino and alkylamino. Acids suitable for this purpose are strong inorganic and organic acids, for example HCl, HBr, $H_2SO_4$ or $HNO_3$. Preferred esters are the alkyl esters, in particular the $C_1-C_{10}$-alkyl esters, such as methyl esters.

Whenever the term "acyl radical" is used in the abovementioned description, this means the radical of an organic acid which is formally formed by removing an OH group from the organic acid, for example the radical of a carboxylic acid and radicals of acids derived therefrom, such as thiocarboxylic acid, unsubstituted or N-substituted iminocarboxylic acids or the radicals of carbonic monoesters, unsubstituted or N-substituted carbaminic acids, sulfonic acids, sulfinic acids, phosphonic acids, phosphinic acids.

An acyl radical is preferably formyl or acyl from the group consisting of CO—$R^Z$, CS—$R^Z$, CO—$OR^Z$, CS—$OR^Z$, CS—$SR^Z$, $SOR^Z$ and $SO_2R^Z$, where $R^Z$ is in each case a $C_1-C_{10}$-hydrocarbon radical, such as $C_1-C_{10}$-alkyl or $C_6-C_{10}$-aryl, which is unsubstituted or substituted, for example by one or more substituents from the group consisting of halogen, such as F, Cl, Br, I, alkoxy, haloalkoxy, hydroxyl, amino, nitro, cyano and alkylthio, or $R^Z$ is aminocarbonyl or aminosulfonyl, where the two lastmentioned radicals are unsubstituted, N-monosubstituted or N,N-disubstituted, for example by substituents from the group consisting of alkyl and aryl.

Acyl is, for example, formyl, haloalkylcarbonyl, alkylcarbonyl, such as $(C_1-C_4)$-alkylcarbonyl, phenylcarbonyl, where the phenyl ring may be substituted, or alkyloxycarbonyl, such as $(C_1-C_4)$-alkyloxycarbonyl, phenyloxycarbonyl, benzyloxycarbonyl, alkylsulfonyl, such as $(C_1-C_4)$-alkylsulfonyl, alkylsulfinyl, such as $C_1-C_4$-(alkylsulfinyl), N-alkyl-1-iminoalkyl, such as N—$(C_1-C_4)$-1-imino-$(C_1-C_4)$-alkyl, and other radicals of organic acids.

A hydrocarbon radical is a straight-chain, branched or cyclic and saturated or unsaturated aliphatic or aromatic hydrocarbon radical, for example alkyl, alkenyl, alkynyl, cycloalkyl, cycloalkenyl or aryl.

A hydrocarbon radical has preferably 1 to 40 carbon atoms, with preference 1 to 30 carbon atoms; with particular preference, a hydrocarbon radical is alkyl, alkenyl or alkynyl having up to 12 carbon atoms or cycloalkyl having 3, 4, 5, 6 or 7 ring atoms or phenyl.

Aryl is a mono-, bi- or polycyclic aromatic system, for example phenyl, naphthyl, tetrahydronaphthyl, indenyl, indanyl, pentalenyl, fluorenyl and the like, preferably phenyl.

A heterocyclic radical or ring (heterocyclyl) can be saturated, unsaturated or heteroaromatic and unsubstituted or substituted; it preferably contains one or more heteroatoms in the ring, preferably from the group consisting of N, O and S; it is preferably an aliphatic heterocyclyl radical having 3 to 7 ring atoms or a heteroaromatic radical having 5 or 6 ring atoms and contains 1, 2 or 3 heteroatoms. The heterocyclic radical can, for example, be a heteroaromatic radical or ring (heteroaryl), such as, for example, a mono-, bi- or polycyclic aromatic system in which at least one ring contains one or more heteroatoms, for example pyridyl, pyrimidinyl, pyridazinyl, pyrazinyl, triazinyl, thienyl, thiazolyl, oxazolyl, furyl, pyrrolyl, pyrazolyl and imidazolyl, or it is a partially or fully hydrogenated radical, such as oxiranyl, oxetanyl, pyrrolidyl, piperidyl, piperazinyl, triazolyl, dioxolanyl, morpholinyl, tetrahydrofuryl. Preference is given to pyrimidinyl and triazinyl. Suitable substituents for a substituted heterocyclic radical are the substituents mentioned further below, and additionally also oxo. The oxo group may also be present at the hetero ring atoms, which may exist in different oxidation states, for example in the case of N and S.

Substituted radicals, such as substituted hydrocarbon radicals, for example substituted alkyl, alkenyl, alkynyl, aryl, phenyl and benzyl, or substituted heterocyclyl or heteroaryl, are, for example, a substituted radical which is derived from an unsubstituted parent compound, where the substituents are, for example, one or more, preferably 1, 2 or 3, radicals from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl and, in the case of cyclic radicals, also alkyl and haloalkyl, and unsaturated aliphatic radicals which correspond to the saturated hydrocarbon-containing radicals mentioned, such as alkenyl, alkynyl, alkenyloxy, alkynyloxy, etc. Among the radicals with carbon atoms, preference is given to those having 1 to 4 carbon atoms, in particular 1 or 2 carbon atoms. Preference is generally given to substituents from the group consisting of halogen, for example fluorine and chlorine, ($C_1$-$C_4$)-alkyl, preferably methyl or ethyl, ($C_1$-$C_4$)-haloalkyl, preferably trifluoromethyl, ($C_1$-$C_4$)-alkoxy, preferably methoxy or ethoxy, ($C_1$-$C_4$)-haloalkoxy, nitro and cyano. Particular preference is given here to the substituents methyl, methoxy and chlorine.

Unsubstituted or substituted phenyl is preferably phenyl which is unsubstituted or mono- or polysubstituted, preferably substituted up to three times, by identical or different radicals, preferably from the group consisting of halogen, ($C_1$-$C_4$)-alkyl, ($C_1$-$C_4$)-alkoxy, ($C_1$-$C_4$)-haloalkyl, ($C_1$-$C_4$)-haloalkoxy and nitro, for example o-, m- and p-tolyl, dimethylphenyl, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl. Cycloalkyl is a carbocyclic saturated ring system having preferably 3-6 carbon atoms, for example cyclopropyl, cyclobutyl, cyclopentyl or cyclohexyl.

The carbon skeleton of the carbon-containing radicals, such as alkyl, alkoxy, haloalkyl, haloalkoxy, alkylamino and alkylthio and the corresponding unsaturated and/or substituted radicals in each case be straight-chain or branched. In these radicals, preference is given to the lower carbon skeletons having, for example, 1 to 6 carbon atoms and, in the case of unsaturated groups, 2 to 6 carbon atoms, unless specified otherwise. Alkyl radicals, also in the composite meanings such as alkoxy, haloalkyl, etc., are, for example, methyl, ethyl, n- or isopropyl, n-, iso-, t- or 2-butyl, pentyls, hexyls, such as n-hexyl, isohexyl and 1,3-dimethylbutyl, heptyls, such as n-heptyl, 1-methylhexyl and 1,4-dimethylpentyl; alkenyl and alkynyl radicals have the meaning of the possible unsaturated radicals which correspond to the alkyl radicals; alkenyl is, for example, allyl, 1-methylprop-2-en-1-yl, 2-methyl-prop-2-en-1-yl, but-2-en-1-yl, but-3-en-1-yl, 1-methyl-but-3-en-1-yl and 1-methyl-but-2-en-1-yl; alkynyl is, for example, propargyl, but-2-yn-1-yl, but-3-yn-1-yl, 1-methyl-but-3-yn-1-yl. Halogen is, for example, fluorine, chlorine, bromine or iodine. Haloalkyl, -alkenyl and -alkynyl is alkyl, alkenyl and alkynyl, respectively, which is partially or fully substituted by halogen, preferably by fluorine, chlorine and/or bromine, in particular by fluorine or chlorine, for example $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other halogen-substituted radicals.

From among the active compounds from the group of the sulfonamides and their salts (component a) very particular preference is given to propoxycarbazone and its sodium salt (propoxycarbazone-methyl sodium), methyl 4-[(4,5-dihydro-3-methoxy-4-methyl-5-oxo-1H-1,2,4-triazol-1-yl)carboxamidosulfonyl]-5-methylthiophene-3-carboxylate and its sodium salt, amidosulfuron and its sodium salt (amidosulfuron-methyl sodium), iodosulfuron-methyl and its sodium salt (iodosulfuron-methyl sodium), foramsulfuron and its sodium salt, thifensulfuron-methyl and its sodium salt and also mesosulfuron-methyl and its sodium salt.

The formulations according to the invention comprise the active compounds from the group of the sulfonamides and their salts (component a) in general in amounts of from 0.1 to 70% by weight, preferably from 0.3 to 60% by weight, particularly preferably from 0.5 to 50% by weight; here and in the entire description, the term "% by weight" (percent by weight) refers to the relative weight of the component in question based on the total weight of the formulation, unless defined otherwise.

The carrier materials (component b) in the formulations according to the invention may originate from a group comprising minerals, carbonates, sulfates and phosphates of alkaline earth metals and earth metals, such as calcium carbonate, polymeric carbohydrates, tectosilicates (framework silicates), such as precipitated silicic acids with low absorbency, and natural tectosilicates, such as kaolin.

Typical representatives of suitable carrier materials are, inter alia, ®Agsorb LVM-GA (attapulgite), ®Harborlite 300 (perlite), ®Collys HV (modified starch), ®Omya chalk (calcium carbonate), ®Extrusil (precipitated silicic acid), ®Kaolin Tec 1 (kaolin, aluminum hydrosilicate), ®Steamic 00S (talc, magnesium silicate).

Preference is given here to natural tectosilicates and calcium carbonate types, such as ®Omya chalk (calcium carbonate), ®Tec1 (kaolin) and ®Harborlite 300 (perlite), and particular preference is given to natural tectosilicates, such as ®Kaolin Tec 1 (kaolin, aluminum hydrosilicate) and ®Harborlite 300 (perlite).

The proportion of carrier materials in the formulations according to the invention (component b) can be 0.1-90% by weight, preferably 5-50% by weight, particularly preferably 10-30% by weight.

The wetting agents from the group of the naphthalenesulfonic acids and the group of the sulfosuccinic acid derivatives and the salts of these groups (component c) in the formulations according to the invention can be selected from a group comprising firstly mono- and diesters of sulfosuccinic acid and their salts (sulfosuccinates) and secondly alkylated naphthalenesulfonic acids and their salts.

Typical representatives of suitable wetting agents are, inter alia, ®Aerosol OTB (dioctylsulfosuccinate), ®Morwet EFW (alkylated naphthalenesulfonates), ®Nekal BX (alkylated naphthalenesulfonates), ®Galoryl MT 804 (alkylated naphthalene-sulfonates).

Preference is given here to the salts of the alkylated naphthalenesulfonic acids and the salts of dioctylsulfosuccinic acid, and particular preference is given to the sodium salts of alkylated naphthalenesulfonates, such as, for example, ®Morwet EFW, and the sodium salts of dioctylsulfosuccinic acid, such as, for example, ®Aerosol OTB.

The proportion of wetting agents in the formulations according to the invention (component c) can be 0.1-50% by weight, preferably 0.25-30% by weight, particularly preferably 0.5-30% by weight.

The further customary auxiliaries and additives (component d) which may be present, if appropriate, in the formulations according to the invention include, for example, dispersants, disintegrating agents, antifoam agents and tackifiers.

Suitable dispersants can be selected from the group consisting of ethoxylated triarylphenols, their optionally partial esters with phosphoric acid, ligninsulfonic acids, condensates of aromatic, optionally polycyclic, sulfonic acids (naphthalenesulfonic acid) with formaldehyde, condensates of optionally polycyclic phenols with formaldehyde and Na sulfite, sulfonic acids of polycyclic aromatics, and also the alkali metal, alkaline earth metal and ammonium salts of these compounds. Typical representatives of suitable dispersants are, inter alia, ®Soprophor BSU (phosphated triarylphenolethoxylate), ®Borresperse NA (ligninsulfonate), ®Rapidaminreserve D (condensate of phenol with Na sulfite and formaldehyde), ®Galoryl DT brands (condensate of aromatic sulfonic acids with formaldehyde), ®Morwet D425 (condensate of naphthalenesulfonic acid and formaldehyde).

Preference is given to condensates of aromatic sulfonic acids with formaldehyde and salts thereof, particular preference is given to the sodium salts of naphthalenesulfonic acids with formaldehyde, such as ®Galoryl DT505 and ®Morwet D425 (both condensates of naphthalenesulfonic acid and formaldehyde).

The proportion of dispersants which may optionally be present in the formulations according to the invention may be 1-50% by weight, preferably 5-30% by weight, particularly preferably 10-20% by weight.

Suitable disintegrating agents may be selected from the group of the modified carbohydrates, such as microcrystalline cellulose, and crosslinked polyvinylpyrrolidones.

Typical representatives of suitable disintegrating agents are, inter alia, ®Avicel PH 101 (microcrystalline cellulose), ®Agrimer XLF (crosslinked polyvinylpyrrolidone), ®Disintex 200 (crosslinked polyvinylpyrrolidone).

Preference is given to crosslinked polyvinylpyrrolidones, such as ®Agrimer XLF. The proportion of disintegrating agents which may optionally be present in the formulations according to the invention may be 0.1-50% by weight, preferably 0.5-25% by weight, particularly preferably 1-10% by weight.

Suitable antifoam agents can be selected from the group of the esters of phosphoric acid with lower alcohols, C6-C10-alcohols, silicone surfactants (suspoemulsions of hydrophobicized silicic acid particles in aqueous emulsion concentrates based on liquid silicone surfactants), such as polydimethylsiloxane, and their absorbates on solid carrier material.

Typical representatives of suitable antifoam agents are, inter alia, ®Rhodorsil 432 (silicone surfactant), butyl phosphate, isobutyl phosphate, n-octanol, ®Wacker ASP15 (polydimethylsiloxane, absorbed on a solid carrier), ®Antischaum-Mittel SE (polydimethylsiloxane).

Preferred are suspoemulsions of hydrophobicized silicic acid particles in aqueous emulsion concentrates based on liquid silicone surfactants, such as ®Antischaum-Mittel SE (polydimethylsiloxane), and solid antifoam agents, such as ®Wacker ASP 15 (polydimethylsiloxane).

The active proportion of antifoam agents which may optionally be present in the formulations according to the invention may be 0.1-10% by weight, preferably 0.3-5% by weight, particularly preferably 0.5-3% by weight.

Suitable tackifiers may be selected from the group consisting of polyvinylpyrrolidone (PVP), polyvinyl alcohol, copolymer of PVP and dimethylaminoethyl methacrylate, butylated PVP, copolymer of vinyl chloride and vinyl acetate, Na salt of the copolymer of propenesulfonic acid and partially hydrolyzed vinyl acetate, sodium caseinate, phenol resins, modified cellulose types.

Typical representatives of suitable tackifiers are, inter alia, ®Luviskol (polyvinylpyrrolidone), ®Mowiol (polyvinyl alcohol), ®Tylose (modified cellulose).

Preference is given to polyvinylpyrrolidone types, particular preference is given to types of low molecular weight, such as ®Luviskol K30.

The proportion of tackifiers which may optionally be present in the formulations according to the invention may be 0.5-20% by weight, preferably 1-10% by weight, particularly preferably 3-8% by weight.

The active compounds referred to by the term "safeners", which may optionally be present as component (e) are to be understood as meaning compounds which are suitable for reducing phytotoxic actions of active crop protection agents, such as herbicides, on crop plants.

The safeners (component e) are preferably selected from the group consisting of:
a) Compounds of the formulae (S-II) to (S-IV),

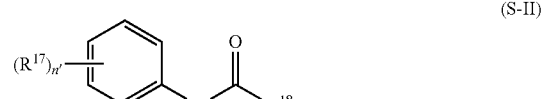
(S-II)

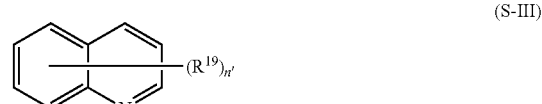
(S-III)

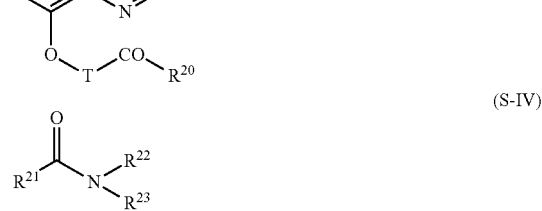
(S-IV)

where the symbols and indices are as defined below:
n' is a natural number from 0 to 5, preferably from 0 to 3;
T is a ($C_1$, or $C_2$)-alkanediyl chain which is unsubstituted or substituted by one or two ($C_1$-$C_4$)-alkyl radicals or by [($C_1$-$C_3$)-alkoxy]carbonyl;
W is an unsubstituted or substituted divalent heterocyclic radical from the group of the partially unsaturated or aromatic five-membered heterocycles having 1 to 3 heteroring atoms of the type N or O, where the ring comprises at least one N-atom and at most one O-atom, preferably a radical from the group consisting of (W1) to (W4),

(W1)

(W2)

(W3)

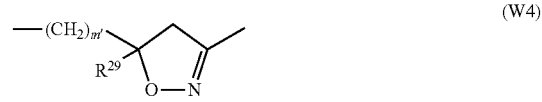
(W4)

m' is 0 or 1;
$R^{17}$, $R^{19}$ are identical or different halogen, ($C_1$-$C_4$)-alkyl, ($C_1$-$C_4$)-alkoxy, nitro or ($C_1$-$C_4$)-haloalkyl radicals;
$R^{18}$, $R^{20}$ are identical or different $OR^{24}$, $SR^{24}$ or $NR^{24}R^{25}$ radicals or a saturated or unsaturated 3- to 7-membered heterocycle having at least one N-atom and up to 3 heteroatoms, preferably from the group consisting of O and S, which is attached via the N-atom to the carbonyl group in (S-II) or (S-III) and which is unsubstituted or substituted by radicals from the group consisting of ($C_1$-$C_4$)-alkyl, ($C_1$-$C_4$)-alkoxy and optionally substituted phenyl, preferably a radical of the formula $OR^{24}$, $NHR^{25}$ or $N(CH_3)_2$, in particular of the formula $OR^{24}$;

$R^{24}$ is hydrogen or an unsubstituted or substituted aliphatic hydrocarbon radical, preferably having a total of 1 to 18 carbon atoms;

$R^{25}$ is hydrogen, ($C_1$-$C_6$)-alkyl, ($C_1$-$C_6$)-alkoxy or substituted or unsubstituted phenyl;

$R^x$ is H, ($C_1$-$C_8$)-alkyl, ($C_1$-$C_8$)-haloalkyl, ($C_1$-$C_4$)-alkoxy-($C_1$-$C_8$)-alkyl, cyano or $COOR^{26}$, where $R^{26}$ is hydrogen, ($C_1$-$C_8$)-alkyl, ($C_1$-$C_8$)-haloalkyl, ($C_1$-$C_4$)-alkoxy-($C_1$-$C_4$)-alkyl, ($C_1$-$C_6$)-hydroxyalkyl, ($C_3$-$C_{12}$)-cycloalkyl or tri-($C_1$-$C_4$)-alkylsilyl;

$R^{27}$, $R^{28}$, $R^{29}$ are identical or different and are hydrogen, ($C_1$-$C_8$)-alkyl, ($C_1$-$C_8$)-haloalkyl, ($C_3$-$C_{12}$)-cycloalkyl or substituted or unsubstituted phenyl;

$R^{21}$ is ($C_1$-$C_4$)-alkyl, ($C_1$-$C_4$)-haloalkyl, ($C_2$-$C_4$)-alkenyl, ($C_2$-$C_4$)-haloalkenyl, ($C_3$-$C_7$)-cycloalkyl, preferably dichloromethyl;

$R^{22}$, $R^{23}$ are identical or different and are hydrogen, ($C_1$-$C_4$)-alkyl, ($C_2$-$C_4$)-alkenyl, ($C_2$-$C_4$)-alkynyl, ($C_1$-$C_4$)-haloalkyl, ($C_2$-$C_4$)-haloalkenyl, ($C_1$-$C_4$)-alkylcarbamoyl-($C_1$-$C_4$)-alkyl, ($C_2$-$C_4$)-alkenylcarbamoyl-($C_1$-$C_4$)-alkyl, ($C_1$-$C_4$)-alkoxy-($C_1$-$C_4$)-alkyl, dioxolanyl-($C_1$-$C_4$)-alkyl, thiazolyl, furyl, furylalkyl, thienyl, piperidyl, substituted or unsubstituted phenyl, or $R^{22}$ and $R^{23}$ together form a substituted or unsubstituted heterocyclic ring, preferably an oxazolidine, thiazolidine, piperidine, morpholine, hexahydropyrimidine or benzoxazine ring;

preferably safeners from the following subgroups of compounds of the formulae (S-II) to (S-IV):

compounds of the type of the dichlorophenylpyrazoline-3-carboxylic acid (i.e. of the formula (S-II) in which W=(W1) and $(R^{17})_n$=2,4-$Cl_2$), preferably compounds such as ethyl 1-(2,4-dichlorophenyl)-5-(ethoxycarbonyl)-5-methyl-2-pyrazoline-3-carboxylate (II-1, mefenpyr-diethyl), mefenpyr-dimethyl and mefenpyr (II-O), and related compounds, as described in WO-A-91/07874;

derivatives of dichlorophenylpyrazolecarboxylic acid (i.e. of the formula (S-II) in which W=(W2) and $(R^{17})_n$=2,4-$Cl_2$), preferably compounds such as ethyl 1-(2,4-dichlorophenyl)-5-methylpyrazole-3-carboxylate (II-2), ethyl 1-(2,4-dichlorophenyl)-5-isopropylpyrazole-3-carboxylate (II-3), ethyl 1-(2,4-dichlorophenyl)-5-(1,1-dimethylethyl)pyrazole-3-carboxylate (II-4), ethyl 1-(2,4-dichlorophenyl)-5-phenylpyrazole-3-carboxylate (II-5) and related compounds, as described in EP-A-0333131 and EP-A-0269806;

compounds of the type of the triazolecarboxylic acids (i.e. of the formula (S-II) in which W=(W3) and $(R^{17})_n$=2,4-$Cl_2$), preferably compounds such as fenchlorazole-ethyl, i.e. ethyl 1-(2,4-dichlorophenyl)-5-trichloromethyl-(1H)-1,2,4-triazole-3-carboxylate (II-6), and related compounds (see EP-A-0174562 and EP-A-0346620);

compounds of the type of the 5-benzyl- or 5-phenyl-2-isoxazoline-3-carboxylic acid or the 5,5-diphenyl-2-isoxazoline-3-carboxylic acid, such as isoxadifen (II-12), (in which W=(W4)), preferably compounds such as ethyl 5-(2,4-dichlorobenzyl)-2-isoxazoline-3-carboxylate (II-7) or ethyl 5-phenyl-2-isoxazoline-3-carboxylate (II-8) and related compounds, as described in WO-A-91/08202, or ethyl 5,5-diphenyl-2-isoxazoline carboxylate (II-9, isoxadifen-ethyl) or n-propyl 5,5-diphenyl-2-isoxazoline carboxylate (II-10) or ethyl 5-(4-fluorophenyl)-5-phenyl-2-isoxazoline-3-carboxylate (II-11), as described in WO-A-95/07897.

Compounds of the type of the 8-quinolineoxyacetic acid, for example those of the formula (S-III) in which $(R^{19})_n$=5-Cl, $R^{20}$=$OR^{24}$ and T=$CH_2$, preferably the compounds 1-methylhexyl (5-chloro-8-quinolineoxy)acetate (III-1, cloquintocetmexyl), 1,3-dimethylbut-1-yl (5-chloro-8-quinolineoxy)acetate (III-2), 4-allyloxybutyl (5-chloro-8-quinolineoxy)acetate (III-3), 1-allyloxyprop-2-yl (5-chloro-8-quinolineoxy)acetate (III-4), ethyl (5-chloro-8-quinolineoxy)acetate (III-5), methyl (5-chloro-8-quinolineoxy)acetate (III-6), allyl (5-chloro-8-quinolineoxy)acetate (III-7), 2-(2-propylideneiminoxy)-1-ethyl (5-chloro-8-quinolineoxy)acetate (III-8), 2-oxoprop-1-yl (5-chloro-8-quinolineoxy)acetate (III-9), (5-chloro-8-quinolineoxy)acetic acid (III-10) and its salts, as described, for example in WO-A-02/34048, and related compounds, as described in EP-A-0860750, EP-A-0094349 and EP-A-0191736 or EP-A-0492366.

Compounds of the type of the (5-chloro-8-quinolineoxy) malonic acid, i.e. of the formula (S-III) in which $(R^{19})_n$=5-Cl, $R^{20}$=$OR^{24}$, T=-CH(COO-alkyl)-, preferably the compounds diethyl (5-chloro-8-quinolineoxy) malonate (III-11), diallyl (5-chloro-8-quinolineoxy)malonate, methyl ethyl (5-chloro-8-quinolineoxy) malonate and related compounds, as described in EP-A-0582198.

Compounds of the type of the dichloroacetamides, i.e. of the formula (S-IV), preferably: N,N-diallyl-2,2-dichloroacetamide (dichlormid (IV-1), from U.S. Pat. No. 4,137,070), 4-dichloroacetyl-3,4-dihydro-3-methyl-2H-1,4-benzoxazine (IV-2, benoxacor, from EP 0149974), N1, N2-diallyl-N2-dichloroacetylglycinamide (DKA-24 (IV-3), from HU 2143821), 4-dichloroacetyl-1-oxa-4-azaspiro[4,5]decane (AD-67), 2,2-dichloro-N-(1,3-dioxolan-2-ylmethyl)-N-(2-propenyl) acetamide (PPG-1292), 3-dichloroacetyl-2,2,5-trimethyloxazolidine (R-29148, IV4), 3-dichloroacetyl-2,2-dimethyl-5-phenyloxazolidine, 3-dichloroacetyl-2,2-dimethyl-5-(2-thienyl)oxazolidine, 3-dichloroacetyl-5-(2-furanyl)-2,2-dimethyloxazolidine (furilazole (IV-5), MON 13900), 1-dichloroacetylhexahydro-3,3,8a-trimethylpyrrolo[1,2-a]pyrimidine-6(2H)-one (dicyclonon, BAS 145138), b) one or more compounds from the group consisting of:

1,8-naphthalic anhydride, methyl diphenylmethoxyacetate, 1-(2-chlorobenzyl)-3-(1-methyl-1-phenylethyl) urea (cumyluron), O,O-diethyl S-2-ethylthioethyl phosphorodithioate (disulfoton), 4-chlorophenyl methylcarbamate (mephenate), O,O-diethyl O-phenyl phosphorothioate (dietholate), 4-carboxy-3,4-dihydro-2H-1-benzopyran-4-acetic acid (CL-304415, CAS-Regno: 31541-57-8), cyanomethoxyimino(phenyl)acetonitrile (cyometrinil), 1,3-dioxolan-2-ylmethoxyimino(phenyl)acetonitrile (oxabetrinil), 4'-chloro-2,2,2-trifluoroacetophenone O-1,3-dioxolan-2-ylmethyloxime (fluxofenim), 4,6-dichloro-2-phenylpyrimidine (fenclorim), benzyl 2-chloro-4-trifluoromethyl-1,3-thiazole-5-carboxylate (flurazole), 2-dichloromethyl-2-methyl-1,3-dioxolane (MG-191), N-(4-methylphenyl)-N'-(1-methyl-1-phenylethyl)urea (dymron), (2,4-dichlorophenoxy)acetic acid (2,4-D), (4-chlorophenoxy) acetic acid, (R,S)-2-(4-chloro-o-tolyloxy)propionic acid (mecoprop), 4-(2,4-dichlorophenoxy)butyric acid (2,4-DB), (4-chloro-o-tolyloxy)acetic acid (MCPA), 4-(4-chloro-o-tolyloxy)butyric acid, 4-(4-chlorophenoxy)butyric acid, 3,6-dichloro-2-methoxybenzoic acid (dicamba), 1-(ethoxycarbonyl)ethyl 3,6-dichloro-2-methoxybenzoate (lactidichlor) and their salts and esters, preferably ($C_1$-$C_8$);

c) N-acylsulfonamides of the formula (S-V) and their salts,

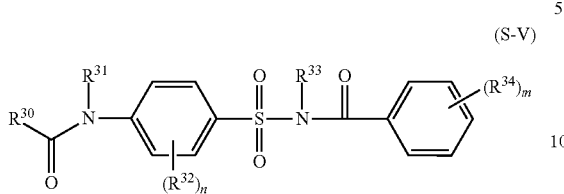

(S-V)

in which $R^{30}$ is hydrogen, a hydrocarbon radical, a hydrocarbonoxy radical, a hydrocarbonthio radical or a heterocyclyl radical which is preferably attached via a C atom, where each of the 4 last-mentioned radicals is unsubstituted or substituted by one or more identical or different radicals from the group consisting of halogen, cyano, nitro, amino, hydroxyl, carboxyl, formyl, carbonamide, sulfonamide and radicals of the formula —$Z^a$—$R^a$, where each hydrocarbon moiety has preferaby 1 to 20 C-atoms and a C-containing radical $R^{30}$ including substituents has preferably 1 to 30 C-atoms;

$R^{31}$ is hydrogen or ($C_1$-$C_4$)-alkyl, preferably hydrogen, or $R^{30}$ and $R^{31}$ together with the group of the formula —CO—N— are the radicals of a 3- to 8-membered saturated or unsaturated ring;

$R^{32}$ are identical or different radicals from the group consisting of halogen, cyano, nitro, amino, hydroxyl, carboxyl, formyl, $CONH_2$, $SO_2NH_2$ or a radical of the formula —$Z^b$—$R^b$;

$R^{33}$ is hydrogen or ($C_1$-$C_4$)-alkyl, preferably H;

$R^{34}$ are identical or different radicals from the group consisting of halogen, cyano, nitro, amino, hydroxyl, carboxyl, CHO, $CONH_2$, $SO_2NH_2$ and a radical of the formula —$Z^c R^c$.

$R^a$ is a hydrocarbon radical or a heterocyclyl radical, where each of the two last-mentioned radicals is unsubstituted or substituted by one or more identical or different radicals from the group consiting of halogen, cyano, nitro, amino, hydroxyl, mono- and di-[($C_1$-$C_4$)-alkyl]amino, or an alkyl radical in which a plurality, preferably 2 or 3, non-adjacent $CH_2$ groups are in each case replaced by an oxygen atom;

$R^b$, $R^c$ are identical or different and are a hydrocarbon radical or a heterocyclyl radical, where each of the two last-mentioned radicals is unsubstituted or substituted by one or more identical or different radicals from the group consisting of halogen, cyano, nitro, amino, hydroxyl, phosphoryl, halo-($C_1$-$C_4$)-alkoxy, mono- and di-[($C_1$-$C_4$)-alkyl]amino, or an alkyl radical in which a plurality, preferably 2 or 3, non-adjacent $CH_2$ groups are in each case replaced by an oxygen atom;

$Z^a$ is a divalent group of the formula —O—, —S—, —CO—, —CS—, —CO—O—, —CO—S—, —O—CO—, —S—CO—, —SO—, —$SO_2$—, —NR*—, —CO—NR*—, —NR*—CO—, —$SO_2$—NR*—or —NR*—$SO_2$—, where the bond indicated on the right-hand side of the divalent group in question is the bond to the radical $R^a$ and where the R* in the 5 last-mentioned radicals independently of one another are each H, ($C_1$-$C_4$)-alkyl or halo-($C_1$-$C_4$)-alkyl;

$Z^b$, $Z^c$ independently of one another are a direct bond or a divalent group of the formula —O—, —S—, —CO—, —CS—, —CO—O—, —CO—S—, —O—CO—, —S—CO—, —SO—, —$SO_2$—, —NR*—, —$SO_2$—NR*—, —NR*$SO_2$—, —CO—NR*—or —NR*—CO—, where the bond indicated on the right-hand side of the divalent group in question is the bond to the radical $R^b$ or $R^c$ and where R* in the 5 last-mentioned radicals independently of one another are each H, ($C_1$-$C_4$)-alkyl or halo-($C_1$-$C_4$)-alkyl;

n is an integer from 0 to 4, preferably 0, 1 or 2, particualrly preferably 0 or 1, and m is an integer from 0 to 5, preferably 0, 1, 2 or 3, in particular 0, 1 or 2; preferably safeners of compounds of the formula (S-V), in which $R^{30}$=$H_3$C—O—$CH_2$—, $R^{31}$=$R^{33}$=H, $R^{34}$=2-OMe (V-1), $R^{30}$=$H_3$C—O—$CH_2$—, $R^{31}$=$R^{33}$=H, R34=2-OMe-5-Cl (V-2), $R^{30}$=cyclopropyl, $R^{31}$=$R^{33}$=H, $R^{34}$=2-OMe (V-3), $R^{30}$=cyclopropyl, $R^{31}$=$R^{33}$=H, R34=2-OMe-5-Cl (V-4), $R^{30}$=cyclopropyl, $R^{31}$=$R^{33}$=H, R34=2-Me (V-5), $R^{30}$=tert-butyl, $R^{31}$=$R^{33}$=H, R34=2-OMe (V-6).

d) Acylsulfamoylbenzamides of the general formula (S-VI), if appropriate also in salt form,

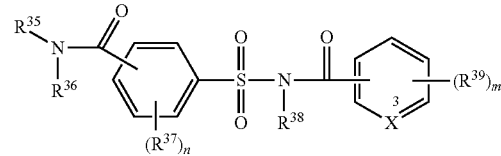

(S-VI)

in which $X^3$ is CH or N;

$R^{35}$ is hydrogen, heterocyclyl or a hydrocarbon radical where the two last-mentioned radicals are optionally substituted by one or more identical or different radicals from the group consisting of halogen, cyano, nitro, amino, hydroxyl, carboxyl, CHO, $CONH_2$, $SO_2NH_2$ and $Z^a$—$R^a$;

$R^{36}$ is hydrogen, hydroxyl, ($C_1$-$C_6$)-alkyl, ($C_2$-$C_6$)-alkenyl, ($C_2$-$C_6$)-alkynyl, ($C_1$-$C_6$)-alkoxy, ($C_2$-$C_6$)-alkenyloxy, where the five last-mentioned radicals are optionally substituted by one or more identical or different radicals from the group consisting of halogen, hydroxyl, ($C_1$-$C_4$)-alkyl, ($C_1$-$C_4$)-alkoxy and ($C_1$-$C_4$)-alkylthio, or $R^{35}$ and $R^{36}$ together with the nitrogen atom that carries them are a 3- to 8-membered saturated or unstaturated ring;

$R^{37}$ is halogen, cyano, nitro, amino, hydroxyl, carboxyl, CHO, $CONH_2$, $SO_2NH_2$ or $Z^b$—$R^b$;

$R^{38}$ is hydrogen, ($C_1$-$C_4$)-alkyl, ($C_2$-$C_4$)-alkenyl or ($C_2$-$C_4$)-alkynyl;

$R^{39}$ is halogen, cyano, nitro, amino, hydroxyl, carboxyl, phosphoryl, CHO, $CONH_2$, $SO_2NH_2$ or $Z^c$—$R^c$;

$R^a$ is a ($C_2$-$C_{20}$)-alkyl radical whose carbon chain is interrupted once or more than once by oxygen atoms, is heterocyclyl or a hydrocarbon radical, where the two last-mentioned radicals are optionally substituted by one or more identical or different radicals from the group consisting of halogen, cyano, nitro, amino, hydroxyl, mono- and di-[($C_1$-$C_4$)-alkyl]amino;

$R^b$, $R^c$ are identical or different and are a ($C_2$-$C_{20}$)-alkyl radical whose carbon chain is interrupted once or more than once by oxygen atoms, are heterocyclyl or a hydrocarbon radical, where the two last-mentioned radicals are optionally substituted by one or more identical or different radicals from the group consisting of halogen, cyano, nitro, amino, hydroxyl, phosphoryl, ($C_1$-$C_4$)-haloalkoxy, mono- and di-[($C_1$-$C_4$)-alkyl]amino $Z^a$ is a divalent unit from the group consisting of O, S, CO, CS, C(O)O, C(O)S, SO, $SO_2$, $NR^d$, C(O)$NR^d$ and $SO_2NR^d$;

$Z^b$, $Z^c$ are identical or different and are a direct bond or divalent unit from the group consisting of O, S, CO, CS, C(O)O, C(O)S, SO, $SO_2$, $NR^d$, $SO_2NR^d$ and C(O)$NR^d$;

$R^d$ is hydrogen, ($C_1$-$C_4$)-alkyl or ($C_1$-$C_4$)-haloalkyl;

n is an integer from 0 to 4, and m, if X is CH is an integer from 0 to 5, and if X is N, is an integer from 0 to 4; preferably safeners of compounds of the formula (S-VI) in which $X^3$ is CH;

$R^{35}$ is hydrogen, ($C_1$-$C_6$)-alkyl, ($C_3$-$C_6$)-cycloalkyl, ($C_2$-$C_6$)-alkenyl, ($C_5$-$C_6$)-cycloalkenyl, phenyl or 3- to 6-membered heterocyclyl having up to three heteroatoms from the group consisting of nitrogen, oxygen and sulfur, where the six last-mentioned radicals are optionally substituted by one or more identical or different substituents from the group consisting of halogen, ($C_1$-$C_6$)-alkoxy, ($C_1$-$C_6$)-haloalkoxy, ($C_1$-$C_2$)-alkylsulfinyl, ($C_1$-$C_2$)-alkylsulfonyl, ($C_3$-$C_6$)-cycloalkyl, ($C_1$-$C_4$)-alkoxycarbonyl, ($C_1$-$C_4$)-alkylcarbonyl and phenyl and, in the case of cyclic radicals, also ($C_1$-$C_4$)-alkyl and ($C_1$-$C_4$)-haloalkyl;

$R^{36}$ is hydrogen, ($C_1$-$C_6$)-alkyl, ($C_2$-$C_6$)-alkenyl, ($C_2$-$C_6$)-alkynyl, where the three last-mentioned radicals are optionally substituted by one or more identical or different substituents from the group consisting of halogen, hydroxyl, ($C_1$-$C_4$)-alkyl, ($C_1$-$C_4$)-alkoxy and ($C_1$-$C_4$)-alkylthio;

$R^{37}$ is halogen, ($C_1$-$C_4$)-haloalkyl, ($C_1$-$C_4$)-haloalkoxy, nitro, ($C_1$-$C_4$)-alkyl, ($C_1$-$C_4$)-alkoxy, ($C_1$-$C_4$)-alkylsulfonyl, ($C_1$-$C_4$)-alkoxycarbonyl or ($C_1$-$C_4$)-alkylcarbonyl;

$R^{38}$ is hydrogen;

$R^{39}$ is halogen, nitro, ($C_1$-$C_4$)-alkyl, ($C_1$-$C_4$)-haloalkyl, ($C_1$-$C_4$)-haloalkoxy, ($C_3$-$C_6$)-cycloalkyl, phenyl, ($C_1$-$C_4$)-alkoxy, cyano, ($C_1$-$C_4$)-alkylthio, ($C_1$-$C_4$)-alkylsulfinyl, ($C_1$-$C_4$)-alkylsulfonyl, ($C_1$-$C_4$)-alkoxycarbonyl or ($C_1$-$C_4$)-alkylcarbonyl;

n is 0, 1 or 2 and m is 1 or 2.

e) compounds of the type of the acylsulfamoylbenzamides, for example of the formula (S-VII) below, which are known, for example from WO-A-99/16744,

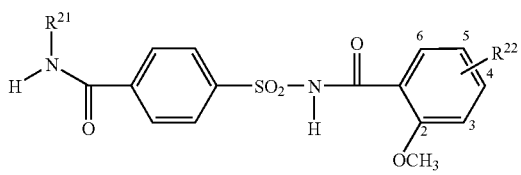

(S-VII)

preferably safeners of the formula (S-VII) in which $R^{21}$=cyclopropyl and $R^{22}$=H (S3-1=4-cyclopropylaminocarbonyl-N-(2-methoxybenzoyl) benzenesulfonamide), $R^{21}$=cyclopropyl and $R^{22}$=5-Cl (S3-2), $R^{21}$=ethyl and $R^{22}$=H (S3-3), $R^{21}$=isopropyl and $R^{22}$=5-Cl (S3-4) and $R^{21}$=isopropyl and $R^{22}$=H (S3-5 =4-isopropylaminocarbonyl-N-(2-methoxybenzoyl) benzenesulfonamide);

f) compounds of the type of the N-acylsulfamoylphenylureas of the formula (S-VIII), which are known, for example, from EP-A-365484,

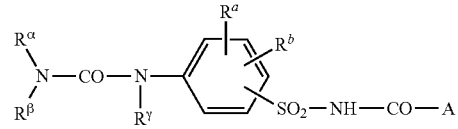

(S-VIII)

in which

A is a radical from the group consisting of

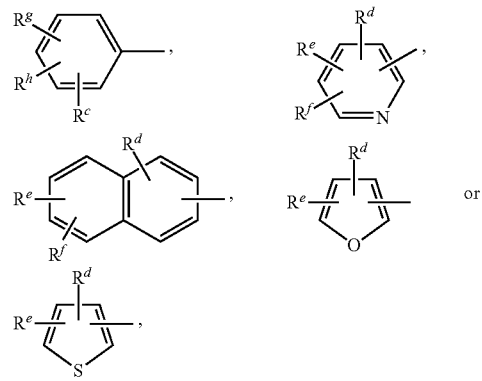

$R^\alpha$ and $R^\beta$ independently of one another are hydrogen, $C_1$-$C_8$-alkyl, $C_3$-$C_8$-cycloalkyl, $C_3$-$C_6$-alkenyl, $C_3$-$C_6$-alkynyl,

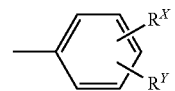

or $C_1$-$C_4$-alkoxy which is substituted by

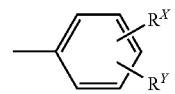

or $C_1$-$C_4$-alkoxy, or $R^\alpha$ and $R^\beta$ together are a $C_4$-$C_6$-alkylene bridge or a $C_4$-$C_6$-alkylene bridge which is interrupted by oxygen, sulfur, SO, $SO_2$, NH or —N($C_1$-$C_4$-alkyl)-, $R^\gamma$ is hydrogen or $C_1$-$C_4$-alkyl, $R^a$ and $R^b$ independently of one another are hydrogen, halogen, cyano, nitro, trifluoromethyl, $C_1$-$C_4$-alkyl, $C_1$-$C_4$-alkoxy, $C_1$-$C_4$-alkylthio, $C_1$-$C_4$-alkylsulfinyl, $C_1$-$C_4$-alkylsulfonyl, —COO$R^j$, —CONR$^k$R$^m$, —COR$^n$, —SO$_2$NR$^k$R$^m$ or —OSO$_2$—$C_1$-$C_4$-alkyl, or $R^a$ and $R^b$ together are a $C_3$-$C_4$-alkylene bridge which may be substituted by halogen or $C_1$-$C_4$-alkyl, or a $C_3$-$C_4$-alkenylene bridge which may be substituted by halogen or $C_1$-$C_4$-alkyl, or a $C_4$-alkadienylene bridge which may be substituted by halogen or $C_1$-$C_4$-alkyl, and $R^g$ and $R^h$ independently of one another are hydrogen, halogen, $C_1$-$C_4$-alkyl, trifluoromethyl, methoxy, methylthio or —COOR$^j$, where $R^e$ is hydrogen, halogen, $C_1$-$C_4$-alkyl or methoxy, $R^d$ is hydrogen, halogen, nitro, $C_1$-$C_4$-alkyl, $C_1$-$C_4$-alkoxy, $C_1$-$C_4$-alkylthio, $C_1$-$C_4$-alkylsulfinyl, $C_1$-$C_4$-alkylsulfonyl, —COOR$^j$ or —CONR$^k$R$^m$, $R^e$ is hydrogen, halogen, $C_1$-$C_4$-alkyl, —COOR$^j$, trifluoromethyl or methoxy, or $R^d$ and $R^e$ together are a $C_3$-$C_4$-alkylene bridge, $R^f$ is hydrogen, halogen or $C_1$-$C_4$-alkyl, $R^x$ and $R^y$ independently of one another are hydrogen, halogen, $C_1$-$C_4$-alkyl, $C_1$-$C_4$-alkoxy, $C_1$-$C_4$-alkylthio, —COOR$^4$, trifluoromethyl, nitro or cyano, $R^j$, $R^k$ and $R^m$ independently of one another are hydrogen or $C_1$-$C_4$-alkyl, $R^k$ and $R^m$ together are a $C_4$-$C_6$-alkylene bridge or a $C_4$-$C_6$-alkylene bridge which is interrupted by oxygen, NH or —N($C_1$-$C_4$-alkyl)-, and $R^n$ is $C_1$-$C_4$-alkyl, phenyl or phenyl which is substituted by halogen, $C_1$-$C_4$-alkyl, methoxy, nitro or trifluoromethyl; preferred safeners of the formula (S-VIII) are 1-[4-(N-2-methoxybenzoyisulfamoyl)phenyl]-3-methylurea, 1-[4-(N-2-methoxybenzoylsulfamoyl)phenyl]-3,3-dimethylurea, 1-[4-(N-4,5-dimethylbenzoyisulfamoyl)phenyl]-3-methylurea, 1-[4-(N-naphthoylsulfamoyl)phenyl]-3,3-dimethylurea, including the stereoisomers and the agriculturally customary salts.

Unless specifically defined otherwise, the following definitions generally apply to the radicals in the formulae (S-II) to (S-VIII).

In the carbon skeleton, the radicals alkyl, alkoxy, haloalkyl, haloalkoxy, alkylamino and alkylthio and the corresponding unsaturated and/or substituted radicals may in each case be straight-chain or branched.

Alkyl radicals, including in the composite meanings, such as alkoxy, haloalkyl, etc., preferably have 1 to 4 C-atoms and are, for example, methyl, ethyl, n- or isopropyl, n-, iso-, tert- or 2-butyl. Alkenyl and alkynyl radicals have the meaning of the unsaturated radicals which are possible and correspond to the alkyl radicals; alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl is, for example, propargyl, but-2-yn-1-yl, but-3-yn-1-yl, 1-methylbut-3-yn-1-yl. "($C_1$-$C_4$)-alkyl" is the short notation of alkyl having 1 to 4 C-atoms; this applies correspondingly to other general radical definitions where the ranges of the possible number of C-atoms are indicated in brackets.

Cycloalkyl is preferably a cyclic alkyl radical having 3 to 8, preferably 3 to 7, particularly preferably 3 to 6, C-atoms, for example cyclopropyl, cyclobutyl, cyclopentyl and cyclohexyl. Cycloalkenyl and cycloalkynyl refer to the corresponding unsaturated compounds.

Halogen is fluorine, chlorine, bromine or iodine. Haloalkyl, haloalkenyl and haloalkynyl are alkyl, alkenyl and alkynyl, respectively, which are partially or fully substituted by halogen, preferably by fluorine, chlorine and/or bromine, in particular by fluorine or chlorine, for example $CF_3$, $CHF_2$, $CH_2F$, $CF_2CF_3$, $CH_2CHFCl$, $CCl_3$, $CHCl_2$, $CH_2CH_2Cl$. Haloalkoxy is, for example, $OCF_3$, $OCHF_2$, $OCH_2F$, $OCF_2CF_3$, $OCH_2CF_3$ and $OCH_2CH_2Cl$. This applies correspondingly to other halogen-substituted radicals.

A hydrocarbon radical may be an aromatic or an aliphatic hydrocarbon radical, where an aliphatic hydrocarbon radical is generally a straight-chain or branched saturated or unsaturated hydrocarbon radical having preferably 1 to 18, particularly preferably 1 to 12, C-atoms, for example alkyl, alkenyl or alkynyl.

An aliphatic hydrocarbon radical is preferably alkyl, alkenyl or alkynyl having up to 12 C-atoms; this applies correspondingly to an aliphatic hydrocarbon radical in a hydrocarbonoxy radical.

Aryl is generally a mono-, bi- or polycyclic aromatic system having preferably 6-20 C-atoms, with preference 6 to 14 C-atoms, particularly preferably 6 to 10 C-atoms, for example phenyl, naphthyl, tetrahydronaphthyl, indenyl, indanyl, pentalenyl and fluorenyl, particularly preferably phenyl.

A heterocyclic ring, heterocyclic radical or heterocyclyl is a mono-, bi- or polycyclic ring system which is saturated, unsaturated and/or aromatic and contains one or more, preferably 1 to 4, heteroatoms, preferably from the group consisting of N, S and O.

Preference is given to saturated heterocycles having 3 to 7 ring atoms and one or two heteroatoms from the group consisting of N, O and S, where the chalcogenes are not adjacent. Particular preference is given to monocyclic rings having 3 to 7 ring atoms and one heteroatom from the group consisting of N, O and S, and also to morpholine, dioxolane, piperazine, imidazoline and oxazolidine. Very particularly preferred saturated heterocycles are oxirane, pyrrolidone, morpholine and tetrahydrofuran. Preference is also given to partially unsaturated heterocycles having 5 to 7 ring atoms and one or two heteroatoms from the group consisting of N, O and S. Particular preference is given to partially unsaturated heterocycles having 5 or 6 ring atoms and one heteroatom from the group consisting of N, O and S. Very particularly preferred partially unsaturated heterocycles are pyrazoline, imidazoline and isoxazoline.

Preference is also given to heteroaryl, for example mono- or bicyclic aromatic heterocycles having 5 to 6 ring atoms which contain one to four heteroatoms from the group consisting of N, O, S, where the chalcogenes are not adjacent. Particular preference is given to monocyclic aromatic heterocycles having 5 or 6 ring atoms which contain a heteroatom from the group consisting of N, O and S, and also pyrimidine, pyrazine, pyridazine, oxazole, thiazole, thiadiazole, oxadiazole, pyrazole, triazole and isoxazole. Very particular preference is given to pyrazole, thiazole, triazole and furan.

Substituted radicals, such as substituted hydrocarbon radicals, for example substituted alkyl, alkenyl, alkynyl, aryl, such as phenyl, and arylalkyl, such as benzyl, or substituted heterocyclyl are a substituted radical derived from the unsubstituted skeleton, where the substituents are preferably one or more, preferably 1, 2 or 3, in the case of Cl and F also up to the maximum possible number, of substituents from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino, mono- and dialkylamino and alkylsulfinyl, haloalkylsulfinyl, alkylsulfonyl, haloalkylsulfonyl and, in the case of cyclic radicals, also alkyl and haloalkyl, and also unsaturated aliphatic substituents corresponding to the saturated hydrocarbon-containing substituents mentioned, preferably alkenyl, alkynyl, alkenyloxy, alkynyloxy. In the case of radicals having C-atoms, preference is given to those having 1 to 4 C-atoms, in particular 1 or 2 C-atoms. In general, preference is given to substituents from the group consisting of halogens, for example, fluorine or chlorine, ($C_1$-$C_4$)-alkyl, preferably methyl or ethyl, ($C_1$-$C_4$)-haioalkyl, preferably trifluoromethyl, ($C_1$-$C_4$)-alkoxy, preferably methoxy or ethoxy, ($C_1$-$C_4$)-haloalkoxy, nitro and cyano. Particular preference is given here to the substituents methyl, methoxy and chlorine.

Mono- or disubstituted amino is a chemically stable radical from the group of the substituted amino radicals which are N-substituted, for example, by one or two identical or different radicals from the group consisting of alkyl, alkoxy, acyl and aryl; preferably monoalkylamino, dialkylamino, acylamino, arylamino, N-alkyl-N-arylamino and also N-heterocycles. Preference is given here to alkyl radicals having 1 to 4 C-atoms. Here, aryl is preferably phenyl. Here, substituted aryl is preferably substituted phenyl. For acyl, the definition given further below applies, preferably $(C_1-C_4)$-alkanoyl. This applies correspondingly to substituted hydroxylamino or hydrazino.

Optionally substituted phenyl is preferably phenyl which is unsubstituted or mono- or polysubstituted, preferably up to trisubstituted, in the case of halogens such as Cl and F also up to pentasubstituted, by identical or different radicals from the group consisting of halogen, $(C_1-C_4)$-alkyl, $(C_1-C_4)$-alkoxy, $(C_1-C_4)$-haloalkyl, $(C_1-C_4)$-haloalkoxy and nitro, for example o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

An acyl radical is a radical of an organic acid having preferably up to 6 C-atoms, for example the radical of a carboxylic acid and radicals of acids derived thereform, such as thiocarboxylic acid, optionally N-substituted iminocarboxylic acids, or the radical of carbonic monoesters, optionally N-substituted carbaminic acids, sulfonic acids, sulfinic acids, phosphonic acids, phosphinic acids. Acyl is, for example, formyl, alkylcarbonyl, such as $(C_1-C_4$-alkyl)carbonyl, phenylcarbonyl, where the phenyl ring may be substituted, for example as indicated above for phenyl, or alkyloxycarbonyl, phenyloxycarbonyl, benzyloxycarbonyl, alkylsulfonyl, alkylsulfinyl or N-alkyl-1-iminoalkyl.

The formulae (S-II) to (S-VIII) also embrace all stereoisomers in which the atoms are linked in the same topological manner, and mixtures thereof. Such compounds contain one or more asymmetric C-atoms or else double bonds, which are not specifically indicated in the general formulae. The possible stereoisomers, defined by their specific spatial form, such as enantiomers, diastereoisomers, Z and E isomers, can be obtained by customary methods from mixtures of the stereoisomers or else be prepared by stereoselective reactions in combination with the use of stereochemically pure starting materials.

The compounds of the formula (S-III) are known, for example, from EP-A-0333131 (ZA-89/1960), EP-A-0269806 (U.S. Pat. No. 4,891,057), EP-A-0346620 (AU-A-89/34951), EP-A-0174562, EP-A-0346620 (WO-A-91/08202), WO-A-91/07874 or WO-A-95/07897 (ZA 94/7120) and the literature cited therein or can be prepared by or analogously to the processes described therein. The compounds of the formula (S-III) are known from EP-A-0086750, EP-A-094349 (U.S. Pat. No. 4,902,340), EP-A-0191736 (U.S. Pat. No. 4,881,966) and EP-A-0492366 and the literature cited therein and can be prepared by or analogously to the processes described therein. Some compounds are furthermore described in EP-A-0582198 and WO-A-02/34048. The compounds of the formula (S-IV) are known from numerous patent applications, for example U.S. Pat. No. 4,021,224 and U.S. Pat. No. 4,021,229. Compounds of the subgroup b) are furthermore known from CN-A-87/102789, EP-A-365484 and also from "The Pesticide Manual", 11th edition, British Crop Protection Council and the Royal Society of Chemistry (1997). The compounds of the subgroup c) are described in WO-A-97/45016, those of subgroup d) in WO-A-99/16744 and those of subgroup e) in EP-A-365484. The publications cited contain details of preparation processes and starting materials and mention preferred compounds. These publications are expressly incorporated into the present description by way of reference.

Particularly preferred safeners (component e) which may optionally be present in the formulations according to the invention are, inter alia: 4-dichloroacetyl-1-oxa-4-azaspiro[4.5]decane (AD-67), 1-dichloroacetylhexahydro-3,3,8a-trimethylpyrrolo[1,2-a]pyrimidin-6(2H)-one (dicyclonon, BAS-145138), 4-dichloroacetyl-3,4-dihydro-3-methyl-2H-1,4-benzoxazine (benoxacor), 1-methylhexyl 5-chloroquinoline-8-oxyacetic acid (cloquintocet-mexyl), α-(cyanomethoxyimino)phenylacetonitrile (cyometrinil), 2,2-dichloro-N-(2-oxo-2-(2-propenylamino)ethyl)-N-(2-propenyl)-acetamide (DKA-24), 2,2-dichloro-N,N-di-2-propenylacetamide (dichlormid), N-(4-methylphenyl)-N'-(1-methyl-1-phenylethyl)urea (dymron), 4,6-dichloro-2-phenylpyrimidine (fenclorim), ethyl 1-(2,4-dichlorophenyl)-5-trichloromethyl-1H-1,2,4-triazole-3-carboxylate (fenchlorazole-ethyl), phenylmethyl 2-chloro-4-trifluoromethyl-thiazole-5-carboxylate (flurazole), 4-chloro-N-(1,3-dioxola n-2-ylmethoxy)-α-trifluoroacetophenonoxime (fluxofenim), 3-dichloroacetyl-5-(2-furanyl)-2,2-dimethyloxazolidine (furilazole, MON-13900), ethyl 4,5-dihydro-5,5-diphenyl-3-isoxazolcarboxylate (isoxadifen-ethyl), diethyl-1-(2,4-dichlorophenyl)-4,5-dihydro-5-methyl-1H-pyrazole-3,5-dicarboxylate (mefenpyr-diethyl), 2-dichloromethyl-2-methyl-1,3-dioxolane (MG-191), 1,8-naphthalic anhydride, a-(1,3-dioxolan-2-ylmethoximino)-phenylacetonitrile (oxabetrinil), 2,2-dichloro-N-(1,3-dioxolan-2-ylmethyl)-N-(2-propenyl)acetamide (PPG-1292), 3-dichloroacetyl-2,2-dimethyloxazolidine(R-28725), 3-dichloroacetyl-2,2,5-trimethyloxazolidine (R-29148), methyl 1-(2-chlorophenyl)-5-phenyl-1H-pyrazole-3-carboxylate, 4-cyclopropylaminocarbonyl-N-(2-methoxybenzoyl)benzenesulfonamide, 4-isopropylaminocarbonyl-N-(2-methoxybenzoyl)benzenesulfonamide and N-(2-methoxybenzoyl)-4-[(methylaminocarbonyl)amino] benzenesulfonamide.

Very particular preference is given to mefenpyr-diethyl, isoxadifen-ethyl, 4-cyclopropylaminocarbonyl-N-(2-methoxybenzoyl)benzenesulfonamide, 4-isopropylaminocarbonyl-N-(2-methoxybenzoyl)benzenesulfonamide, and mefenpyr-diethyl is especially preferred.

The proportion of the safeners (component e) which may optionally be present in the formulations according to the invention is 0.01-50% by weight, preferably 0.1-40% by weight, particularly preferably 5-20% by weight.

When safeners, which may optionally be present in the formulations according to the invention, are used, special solvents (component e-1), emulsifiers (component e-2) and carrier materials (component e-3) are, if appropriate, employed.

Solvents suitable for this purpose (component e-1) are chosen from the group of the aromatic and aliphatic hydrocarbons, esters and amides of organic and inorganic acids, aromatic, aliphatic and cycloaliphatic ketones and alcohols.

Typical representatives of suitable solvents are, inter alia, ®Solvesso types (aromatic hydrocarbon), ®Essobayol (aliphatic hydrocarbon), ®Exxate (esters of organic acids), OHallcomide (amides of organic acids), acetophenone (aromatic ketone), methyl isobutyl ketone (aliphatic ketone), ®Anon (cyclohexanone: cycloaliphatic ketone).

Preference is given to solvents from the group of the aromatic and aliphatic hydrocarbons, such as, for example, ®Solvesso types (aromatic hydrocarbons), and aromatic hydrocarbons, such as ®Solvesso 200 ND (alkylated naphthalene), are particularly preferred.

The proportion of the solvents (component e-1) required, if appropriate, for the addition of safener in the formations according to the invention may be 0.01-50% by weight, preferably 0.5-40%, particularly preferably 5-20% by weight.

Emulsifiers (component e-2) suitable for this purpose may be of anionic and/or nonionic nature and are selected from the group comprising: salts of alkylated aromatic sulfonic acids, optionally alkylated copolymers of alkylene oxides, such as ethylene oxide and propylene oxide (EO/PO), ethoxylated castor oil, fatty-acylated sorbitan ethoxylate, mono- and diglycerides of fatty acids and their salts, fatty acids and their salts, reaction products of optionally aliphatically or aromatically substituted phenols with alkylene oxides, and also, if appropriate, the partial esters of these surfactants with organic acids, such as acetic acid or citric acid, or inorganic acids, such as sulfuric acid or phosphoric acid.

Typical representatives of suitable emulsifiers are, inter alia, ®Phenylsulfonat CA (Ca dodecylbenzenesulfonate), ®Soprophor types (optionally esterified derivatives of tristyrylphenol ethoxylates), ®Emulsogen 3510 (alkylated EO/PO copolymer), ®Emulsogen EL 400 (ethoxylated castor oil), ®Tween types (fatty-acylated sorbitan ethoxylates), ®Calsogen AR 100 (Ca dodecylbenzenesulfonate).

Preference is given to combinations of salts of alkylated aromatic sulfonic acids, such as ®Phenylsulfonat Ca and/or ®Calsogen AR 100, with alkylated copolymers of ethylene oxide and propylene oxide, such as ®Emulsogen 3510.

Particular preference is given to combinations of salts of dodecylbenzenesulfonic acid, such as ®Calsogen AR 100 with alkylated copolymer of ethylene oxide and propylene oxide, such as ®Emulsogen 3510.

The proportion of the emulsifiers (component e-2) required, if appropriate, for the addition of safener in the formulations according to the invention may be 0.01-25% by weight, preferably 0.5-10% by weight, particularly preferably 1-5% by weight.

Carrier materials (component e-3) suitable for this purpose may be selected from the group of the highly absorbent carriers characterized by an absorbency of at least 200 g of dibutyl phthalate per 100 g of carrier material.

Typical representatives of suitable carrier materials are, inter alia, ®Calflo E (calcium silicate) and ®Sipernat types (synthetic precipitated silicic acid of high absorbency).

Preference is given to calcium silicate, such as ®Calflo E, and precipitated silicic acid, such as ®Sipernat 50 S.

The proportion of the carrier materials (component e-3) required, if appropriate, for the addition of safener in the formulations according to the invention may be 0.5-30% by weight, preferably 1-20% by weight, particularly preferably 4-10% by weight.

Suitable agrochemically active compounds (component of, which may be present or not, are, for example, agrochemically active compounds different from components (a) and (e), such as herbicides, fungicides, insecticides, plant growth regulators and the like.

Suitable active compounds different from components (a) and (e) are preferably herbicidally active compounds. Here, mention may be made of herbicides from the group of the carbamates, thiocarbamates, haloacetanilides, substituted phenoxy-, naphthoxy- and phenoxyphenoxycarboxylic acid derivatives and also heteroaryloxy-phenoxyalkanecarboxylic acid derivatives, such as quinolyloxy-, quinoxalyloxy-, pyridyloxy-, benzoxazolyloxy- and benzothiazolyloxyphenoxyalkanecarboxylic acid esters, cyclohexanedione derivatives, phosphorus-containing herbicides, for example of the glufosinate type or the glyphosate type, and also S-(N-aryl-N -alkylcarbamoylmethyl)dithiophosphoric esters, especially, for example:

A) herbicides of the type of the phenoxyphenoxy- and heteroaryloxyphenoxycarboxylic acid derivatives, such as A1) phenoxyphenoxy- and benzyloxyphenoxycarboxylic acid derivatives, for example methyl 2-(4-(2,4-dichlorophenoxy)phenoxy)propionate (diclofop-methyl), methyl 2-(4-(4-bromo-2-chlorophenoxy)phenoxy)propionate (DE-A-2601548), methyl 2-(4-(4-bromo-2-fluorophenoxy)phenoxy)propionate (U.S. Pat No. 4,808,750), methyl 2-(4-(2-chloro4-trifluoromethylphenoxy)phenoxy)propionate (DE-A-2433067), methyl 2-(4-(2-fluoro-4-trifluoromethylphenoxy)phenoxy)propionate (U.S. Pat. No. 4,808,750), methyl 2-(4-(2,4-dichlorobenzyl)phenoxy)propionate (DE-A-2417487), ethyl 4-(4-(4-trifluoromethylphenoxy)phenoxy)pent-2-enoate, methyl 2-(4-(4-trifluoromethylphenoxy)phenoxy)propionate (DE-A-2433067);

A2) "monocyclic" heteroaryloxyphenoxyalkanecarboxylic acid derivatives, for example ethyl 2-(4-(3,5-dichloropyridyl-2-oxy)phenoxy)propionate (EP-A-0002925), propargyl 2-(4-(3,5-dichloropyridyl-2-oxy)phenoxy)propionate (EP-A-0003114), methyl 2-(4-(3-chloro-5-trifluoromethyl-2-pyridyloxy)phenoxy)propionate (EP-A-0003890), ethyl 2-(4-(3-ch loro-5-trifluoromethyl-2-pyridyloxy)phenoxy)propionate (EP-A-0003890), propargyl 2-(4-(5-chloro-3-fluoro-2-pyridyloxy)phenoxy) propionate (EP-A-0191736), butyl 2-(4-(5-trifluoromethyl-2-pyridyloxy)phenoxy)propionate (fluazifop -butyl);

A3) 'bicyclic" heteroaryloxyphenoxyalkanecarboxylic acid derivatives, for example methyl and ethyl 2-(4-(6-chloro-2-quinoxalyloxy)phenoxy)propionate (quizalofopmethyl and quizalofopethyl), methyl 2-(4-(6-fluoro-2-quinoxalyloxy)phenoxy)propionate (see J. Pest. Sci. Vol. 10, 61 (1985)), 2-isopropylideneam inooxyethyl 2-(4-(6-ch loro-2-quinoxalyloxy)phenoxy) propionate (propaquizafop), ethyl 2-(4-(6-chlorobenzoxazol-2-yloxy)phenoxy)propionate (fenoxaprop -ethyl), its D(+) isomer (fenoxaprop-P-ethyl EX) and ethyl 2-(4-(6-chlorobenzothiazol-2-yloxy)-phenoxy)propionate (DE-A-2640730), tetrahydro-2-furylmethyl 2-(4-(6-chloroquinoxalyloxy)phenoxy) propionate (EP-A-0323727);

A4) phenoxycarboxylic acid derivatives, such as 2,4-D, 2,4-DP, 2,4-DB, CMPP and MCPA and their esters and salts;

B) chloroacetanilides, for example N-methoxymethyl-2,6-diethyl-chloroacetanilide (alachlor), N-(3-methoxyprop-2-yl)-2-methyl-6-ethylchloroacetanilide (metolachlor), 2,6-dimethyl-N-(3-methyl-1,2,4-oxadiazol-5-ylmethyl) chloroacetanilide, N-(2,6-dimethylphenyl)-N-(1-pyrazolylmethyl)chloroacetamide (metazachlor);

C) thiocarbamates, for example S-ethyl N,N-dipropylthiocarbamate (EPTC), S-ethyl N,N-diisobutylthiocarbamate (butylate);

D) cyclohexanedione oximes, for example methyl 3-(1-allyloxyiminobutyl)4-hydroxy-6,6-dimethyl-2-oxocyclohex-3-enecarboxylate (alloxydim), 2-(1-ethoxyiminobutyl)-5-(2-ethylthiopropyl)-3-hydroxycyclohex-2-ene-1-one (sethoxydim), 2-(1-ethoxyiminobutyl)-5-(2-phenylthiopropyl)-3-hydroxycyclohex-2-ene-1-one (cloproxydim), 2-(1-(3-chloroallyloxy)iminobutyl)-5-(2-ethylthiopropyl)-3-hydroxycyclohex-2-ene-1-one, 2-(1-(3-chloroallyloxy)iminopropyl)-5-(2-ethylthiopropyl)-3-hydroxycyclohex-2-ene-1-one (clethodim), 2-(1-ethoxyiminobutyl)-3-hydroxy-5-(thian-3-yl)cyclohex-2-enone (cycloxydim), 2-(1-ethoxyiminopropyl)-5-(2,4,6-trimethylphenyl)-3-hydroxycyclohex-2-ene-1-one (tralkoxydim);

E) benzoylcyclohexanediones, for example 2-(2-chloro4-methylsulfonylbenzoyl)cyclohexane-1,3-dione (SC-0051, EP-A-0137963), 2-(2-nitrobenzoyl)4,4-dimethylcyclohexane-1,3-dione (EP-A-0274634), 2-(2-nitro-4-methylsulfonylbenzoyl)4,4-dimethylcyclohexane-1,3-dione (WO-A-91/13548 mesotrione);

F) S—(N-aryl-N-alkylcarbamoylmethyl) dithiophosphonates, such as S—[N-(4-chlorophenyl)-N-isopropylcarbamoylmethyl] O,O-dimethyl dithiophosphate (anilophos);

G) alkylazines, such as, for example, described in WO-A-97/08156, WO-A-97/31904, DE-A- 19826670, WO-A-98/15536, WO-A-98/15537, WO-A-98/15538, WO-A-98/15539 and also DE-A-19828519, WO-A-98/34925, WO-A-98/42684, WO-A-99/18100, WO-A-99/19309, WO-A-99/37627 and WO-A-99/65882, preferably those of the formula (G)

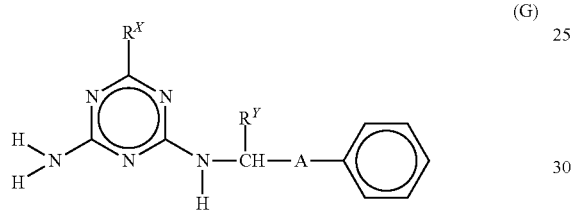

(G)

in which $R^X$ is $(C_1-C_4)$-alkyl or $(C_1-C_4)$-haloalkyl;

$R^Y$ is $(C_1-C_4)$-alkyl, $(C_3-C_6)$-cycloalkyl or $(C_3-C_6)$-cycloalkyl-$(C_1-C_4)$-alkyl and A is —CH$_2$—, —CH$_2$—CH$_2$—, —CH$_2$—CH$_2$—CH$_2$—, —O—, —CH$_2$—CH$_2$—O—, —CH$_2$—CH$_2$—C particularly preferably those of the formulae G1-G7

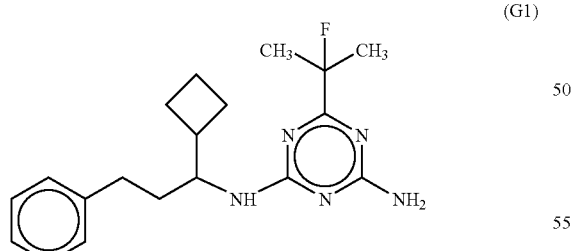

(G1)

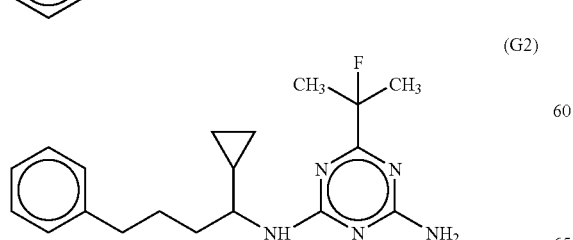

(G2)

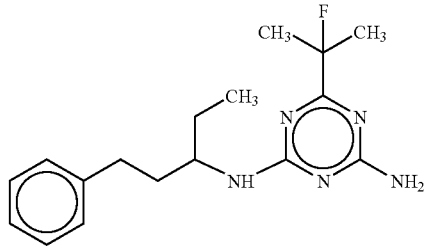

(G3)

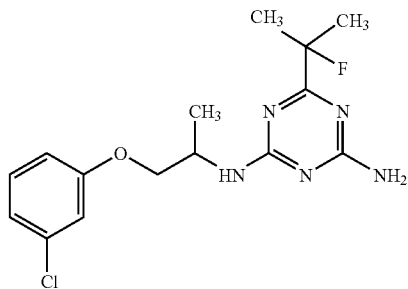

(G4)

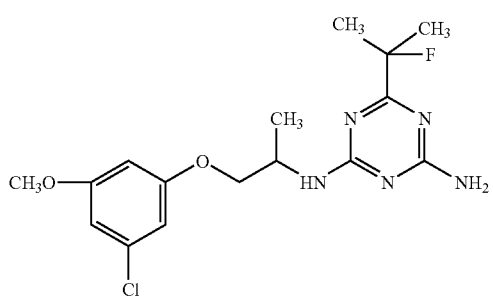

(G5)

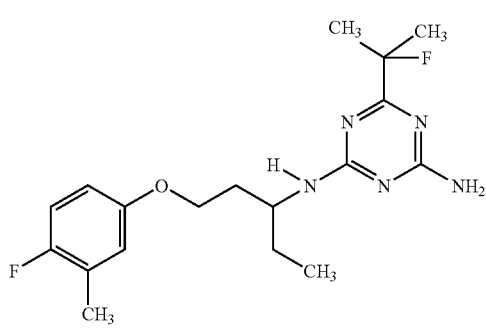

(G6)

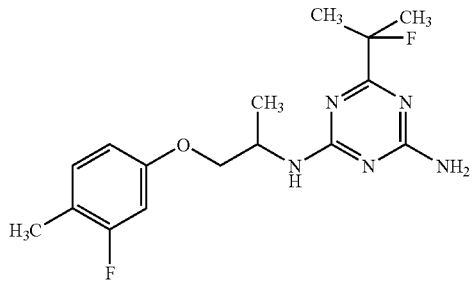

(G7)

H) Phosphorus-containing herbicides, for example of the glusosinate type, such as glufosinate in a narrower sense, i.e. D,L-2-amino-4-[hydroxy(methyl)phosphinyl]-butanoic acid, glufosinate monoammonium salt, L-glufosinate, L- or (2S)-2-amino-4-[hydroxy(methyl)phosphinyl]butanoic acid L-glufosinate monoammonium salt or bialaphos (or bilanafos), i.e. L-2-amino-4-[hydroxy(methyl)phosphinyl]butanoyl-L-alanyl-L-alanine, in particular its sodium salt, or of the glyphosate type, such as glyphosate, i.e. N-(phosphonomethyl)glycine, glyphosate monoisopropylammonium salt, glyphosate sodium salt or sulfosate, i.e. N-(phosphonomethyl)glycine trimesium salt=N-(phosphonomethyl)glycine trimethylsulfoxonium salt.

Also to be mentioned here are imidazolinones, pyrimidinyloxypyridinecarboxylic acid derivatives, pyrimidyloxybenzoic acid derivatives, triazolopyrimidinesulfonamide derivatives with typical representatives such as, for example, diflufenican, bromoxynil-comprising or ioxynil-comprising products, herbicides from the class of the oxyacetamides, such as flufenacet, herbicides from the class of the aryloxyphenoxypropionates, such as fenoxaprop-p-ethyl, beet herbicides, such as desmedipham, phenmedipham, ethofumesate or metamitron, or else active compounds of the class of the HPPD inhibitors (for example isoxaflutole, sulcotrione, mesotrione), especially, for example:

I) imidazolinones, for example methyl 2-(4-isopropyl-4-methyl-5-oxo-2-imidazolin-2-yl)-5-methylbenzoate and 2-(4-isopropyl4-methyl-5-oxo-2-imidazolin-2-yl)4-methylbenzoic acid (imazamethabenz), 5-ethyl-2-(4-isopropyl-4-methyl-5-oxo-2-imidazolin-2-yl)-pyrid ine-3-carboxylic acid (imazethapyr), 2-(4-isopropyl4-methyl-5-oxo-2-imidazolin-2-yl)quinoline-3-carboxylic acid (imazaquin), 2-(4-isopropyl-4-methyl-5-oxo-2-imidazolin-2-yl)pyridine-3-carboxylic acid (imazapyr), 5-methyl-2-(4-isopropyl4-methyl-5-oxo-2-imidazolin-2-yl)pyridine-3-carboxylic acid (imazethamethapyr);

J) triazolopyrimidinesulfonamide derivatives, for example N-(2,6-difluorophenyl)-7-methyl- 1,2,4-triazolo[1,5-c]pyrimidine-2-sulfonamide (flumetsulam), N-(2,6-dichloro-3-methylphenyl)-5,7-dimethoxy-1,2,4-triazolo[1,5-c]pyrimidine-2-sulfonamide, N-(2,6-difluorophenyl)-7-fluoro-5-methoxy-1,2,4-triazolo[1,5-c]pyrimidine-2-sulfonamide, N-(2,6-dichloro-3-methylphenyl)-7-chloro-5-methoxy-1,2,4-triazolo[1,5-c]pyrimidine-2-sulfonamide, N-(2-chloro-6-methoxycarbonyl)-5,7-dimethyl-1,2,4-triazolo[1,5-c]pyrimidine-2-sulfonamide (EP-A-0343752, U.S. Pat. No. 4,988,812);

K) pyrimidinyloxypyridinecarboxylic acid or pyrimidinyloxybenzoic acid derivatives, for example benzyl 3-(4,6-dimethoxypyrimidin-2-yl)oxypyridine-2-carboxylate (EP-A-0249707), methyl 3-(4,6-dimethoxypyrimidin-2-yl)oxypyridine-2-carboxylate (EP-A-0249707), 2,6-bis[(4,6-dimethoxypyrimidin-2-yl)oxy]benzoic acid (EP-A-0321846), 1-ethoxycarbonyloxyethyl 2,6-bis[(4,6-dimethoxypyrimidin-2-yl)oxy ]benzoate (EP-A-0472113).

The herbicides of groups A to K are known, for example, from the abovementioned publications and from "The Pesticide Manual", 12th edition, (2000), The British Crop Protection Council, "Agricultural Chemicals Book II—Herbicides—", by W. T. Thompson, Thompson Publications, Fresno Calif., USA 1990 and "Farm Chemicals Handbook '90", Meister Publishing Company, Willoughby Ohio, USA, 1990.

Suitable agrochemically active compounds (component f) (which are different from components (a) and (e) and may or may not be present) for the formulations according to the invention are, for example, the known active compounds listed below, as described, for example, in Weed Research 26, 441445 (1986), or in "The Pesticide Manual", 12th edition, The British Crop Protection Council (2000), and the literature cited therein, for example in formulated mixtures or as components for tank mixes. The compounds are referred to either by the "common name" according to the International Organization for Standardization (ISO) or by the chemical name, if appropriate together with a customary code number, and include in each case all use forms, such as acids, salts, esters and isomers, such as stereoisomers and optical isomers: acetochlor; acifluorfen; aclonifen; AKH 7088, i.e. [[[1-[5-[2-chloro-4 -(trifluoromethyl)phenoxy]-2-nitrophenyl]-2-methoxyethylidene]amino]oxy]acetic acid and methyl [[[1-[5-[2-chloro4-(trifluoromethyl)phenoxy]-2-nitrophenyl]-2-methoxyethylidene]amino]oxy]acetate; alachlor; alloxydim; ametryn; amitrol; AMS, i.e. ammonium sulfamate; anilofos; asulam; atrazine; azafenidine (DPX-R6447); aziprotryn; barban; BAS 516 H, i.e. 5-fluoro-2-phenyl-4H-3,1-benzoxazin4-one; benazolin; benfluralin; benfuresate; bensulide; bentazone; benzofluor; benzoylprop-ethyl; benzthiazuron; bialaphos; bifenox; bispyribac-sodium (KIH-2023), bromacil; bromobutide; bromofenoxim; bromoxynil, in particular bromoxynil-octanoate and bromoxynil-heptanoate; butachlor; butamifos; butenachlor; buthidazole; butralin; butroxydim (ICl-0500), butylate; cafenstrole (CH-900); carbetamide; cafentrazone; CDM, i.e. 2-chloro-N,N-di-2-propenylacetamide; CDEC, i.e. 2-chloroallyl diethyldithiocarbamate; chlomethoxyfen; chloramben; cloransulam-methyl (XDE-565), chlorazifop-butyl, chlorbromuron; chlorbufam; chlorfenac; chlorflurenol-methyl; chloridazon; chlornitrofen; chlorotoluron; chloroxuron; chlorpropham; chlorthal-dimethyl; chlorthiamid; cinidon-ethyl, cinmethylin; clethodim; clodinafop and its ester derivatives (for example clodinafop-propargyl); clomazone; clomeprop; cloproxydim; clopyralid; cumyluron (JC 940); cyanazine; cycloate; cycloxydim; cycluron; cyhalofop and its ester derivatives (for example the butyl ester, DEH-112); cyperquat; cyprazine; cyprazole; 2,4-D; 2,4-DB; dalapon; desmedipham; desmetryn; di-allate; dicamba; dichlobenil; dichlorprop; diclofop and its esters, such as diclofop-methyl; diclosulam (XDE-564), diethatyl; difenoxuron; difenzoquat; diflufenican; diflufenzopyr-sodium (SAN-835H), dimefuron; dimethachlor; dimethametryn; dimethenamid (SAN-582H); dimidazone, methyl 5-(4, 6-dimethylpyrimidin-2-ylcarbamoylsulfamoyl)-1-(2-pyridyl)pyrazole-4-carboxylate (NC-330); triaziflam (IDH-1105), cinosulfon; dimethipin, dinitramine; dinoseb; dinoterb; diphenamid; dipropetryn; diquat; dithiopyr; diuron; DNOC; eglinazine-ethyl; EL177, i.e. 5-cyano-1-(1,1-dimethylethyl)-N-methyl-1H-pyrazole-4-carboxamide; endothal; indanofan (MK-243), EPTC; esprocarb; ethalfluralin; ethidimuron; ethiozin; ethofumesate; F5231, i.e. N-[2-chloro4-fluoro-5-[4-(3-fluoropropyl)-4,5-dihydro-5-oxo-1H-tetrazol-yl]phenyl]ethanesulfonamide; ethoxyfen and its esters (for example the ethyl ester, HN-252); etobenzanid (HW52); 3-(4-ethoxy-6-ethyl-1,3,5-triazin-2-yl)-1-(2,3-dihydro-1,1-dioxo-2-methylbenzo[b]thiophene-7-sulfonyl)urea (EP-A 079 683); 3-(4-ethyl-6-methoxy-1,3,5-triazin-2-yl)-1-(2,3-dihydro-1,1-dioxo-2-methylbenzo[b]thiophene-7-sulfonyl) urea (EP-A-079683); fenoprop; clomazone, fenoxaprop and fenoxaprop-P and their esters, for example fenoxaprop-P-ethyl and fenoxaprop-ethyl; butroxydimfenuron; flampropmethyl; flufenacet (BAY-FOE-5043), fluazifop and fluazifop-P and their esters, for example fluazifop-butyl and fluazifop-P-butyl, florasulam (DE-570); fluchloralin; flumetsulam; fluometuron; flumiclorac and its esters (for example the pentyl ester, S-23031); flumioxazin (S-482); flumipropyn; flupoxam (KNW-739); fluorodifen; fluoroglycofen-ethyl; flupropacil (UBIC4243); fluridone; flurochloridone; fluroxypyr; flurtamone; fluthiacet-methyl (KIH-9201), fomesafen; fosamine; furyloxyfen; glufosinate; glyphosate; halosafen; haloxyfop and its esters; haloxyfop-P (=R-haloxyfop) and its esters; hexazinone; imazamethabenz-methyl;

imazamox (AC-299263), imazapyr; imazaquin and salts thereof, such as the ammonium salt; imazapic; imazethapyr; ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metam; methazole; methoxyphenone; methyidymron; metobenzuron, metobromuron; metolachlor; S-metolachlor, metosulam (XRD 511); metoxuron; metribuzin; maleic hydrazide; molinate; monalide; monocarbamide dihydrogensulfate; monolinuron; monuron;

MT 128, i.e. 6-chloro-N-(3-chloro-2-propenyl)-5-methyl-N-phenyl -3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nipyraclophen; nitralin; nitrofen; nitrofluorfen; norflurazon; orbencarb; oryzalin; oxadiargyl (RP-020630); oxadiazon; oxaziclomefone (MY-100), oxyfluorfen; paraquat; pebulate; pendimethalin; pentoxazone (KPP-314), perfluidone; phenisopham; phenmedipham; picloram; piperophos; pyributicarb; pirifenop-butyl; pretilachlor; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prynachlor; pyraflufen-ethyl (ET-751), chloridazon; pyrazoxyfen; pyribenzoxim, pyridate; pyriminobac-methyl (KIH-6127), pyrithiobac (KIH-2031); pyroxofop and its esters (for example the propargyl ester); quinclorac; quinmerac; quizalofop, quizalofop and quizalofop-P and their ester derivatives, for example quizalofop-ethyl; quizalofop-P-tefuryl and -ethyl; S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoro-methyl)phenoxy]-2-naphthalenyl]oxy]propanoic acid and methyl 2-[[7-[2-chloro-4-(trifluoromethyl)phenoxy]-2-naphthalenyl]oxy] propanoate; sulfazuron; glyphosate-trimesium (ICl-A0224); TCA; tebutam (GCP-5544); tebuthiuron; tepraloxydim (BAS-620H), terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluron; thiazopyr (Mon-1 3200); thidiazimin (SN-124085); thiobencarb; tiocarbazil; tralkoxydim; tri-allate; triazofenamide; triclopyr; tridiphane; trietazine; trifluralin; trimeturon; tsitodef; vernolate; WL 110547, i.e. 5-phenoxy-1-[3-(trifluoromethyl)phenyl]-1H-tetrazole; UBH-509; D-489; LS 82-556; KPP-300; KPP-421, MT-146, NC-324; butenachlor (KH-218); DPX-N8189; haloxyfop-etotyl (DOWCO-535); DK-8910; flumioxazin (V-53482); PP-600; MBH-001, amicarbazone, aminopyralid, beflubutamid, benzobicyclon, benzofenap, benzfendizone, butafenacil, chlorfenprop, cloprop, daimuron, dichlorprop-P, dimepipeate, dimethenamid-P, fentrazamide, flamprop-M, fluazolate, indanofan, isoxachlortole, isoxaflutole, MCPA-thioethyl, mecoprop-P, mesotrione, metamifop, penoxsulam, pethoxamid, picolinafen, profluazol, profoxydim, pyraclonil, pyrazolynate, pyridafol, pyriftalid, sulcotrione, thidiazuron. The proportion of the agrochemically active compounds (component f) which are different from components (a) and (e) and which may optionally be present in the formulations according to the invention may be 0.1-70% by weight, preferably 0.3-50% by weight, particularly preferably 0.5-30% by weight.

The invention furthermore relates to a herbicidal composition which may be prepared from the formulations according to the invention by dilution with liquids, preferably water.

It may be advantageous to add to the herbicidal compositions obtained in this manner further active compounds, preferably agrochemically active compounds (for example as tank mixing partners in the form of corresponding formulations) and/or auxiliaries and additives customary for application, for example self-emulsifying oils, such as vegetable oils or paraffin oils, and/or fertilizers. Accordingly, the present invention also relates to such compositions, preferably herbicidal compositions, based on the formulations according to the invention.

A particular embodiment of the invention relates to the use of the herbicidal compositions, obtainable from the formulations according to the invention, for controlling unwanted vegetation, hereinbelow referred to as "herbicidal composition". The herbicidal compositions have outstanding herbicidal activity against a broad spectrum of economically important monocotyledonous and dicotyledonous harmful plants. Even perennial weeds which produce shoots from rhizomes, rootstocks or other perennial organs and which are difficult to control are controlled well. In this context, it does not matter whether the herbicidal compositions are applied before sowing, pre-emergence or post-emergence. Specific examples may be mentioned of some representatives of the *monocotyledonous* and *dicotyledonous* weed flora which can be controlled by the herbicidal compositions, without the enumeration being a restriction to certain species.

Examples of weed species on which the herbicidal compositions act efficiently are, from amongst the *monocotyledonous* weed species, *Apera spica venti, Avena* spp., *Alopecurus* spp., *Brachiaria* spp., *Digitaria* spp., *Lolium* spp., *Echinochloa* spp., *Panicum* spp., *Phalaris* spp., *Poa* spp., *Setaria* spp. and *Bromus* spp. such as *Bromus catharticus, Bromus secalinus, Bromus erectus, Bromus tectorum* and *Bromus japonicus*, and *Cyperus* species from the annual group, and, among the *perennial* species, *Agropyron, Cynodon, Imperata* and *Sorghum* and also *perennial Cyperus* species. In the case of the *dicotyledonous* weed species, the spectrum of action extends to genera such as, for example, *Abutilon* spp., *Amaranthus* spp., *Chenopodium* spp., *Chrysanthemum* spp., *Galium* spp. such as *Galium aparine, Ipomoea* spp., *Kochia* spp., *Lamium* spp., *Matricaria* spp., *Pharbitis* spp., *Polygonum* spp., *Sida* spp., *Sinapis* spp., *Solanum* spp., *Stellaria* spp., *Veronica* spp. and *Viola* spp., *Xanthium* spp., among the annuals, and *Convolvulus, Cirsium, Rumex* and *Artemisia* in the case of the perennial weeds.

The compositions according to the invention also act outstandingly efficiently on harmful plants which are found under the specific cultures in rice, such as, for example, *Echinochloa, Sagittaria, Alisma, Eleocharis, Scirpus* and *Cyperus*.

If the herbicidal compositions are applied to the soil surface before germination, the weed seedlings are either prevented completely from emerging or else the weeds grow until they have reached the cotyledon stage, but then their growth stops, and, eventually, after three to four weeks have elapsed, they die completely.

If the herbicidal compositions are applied post-emergence to the green parts of the plants, growth likewise stops drastically a very short time after the treatment, and the weed plants remain at the growth stage of the point of time of application, or they die completely after a certain time, so that in this manner competition by the weeds, which is harmful to the crop plants, is eliminated very early and in a sustained manner.

The herbicidal compositions are distinguished by a rapidly commencing and long-lasting herbicidal action. As a rule, the rainfastness of the active substances in the herbicidal compositions is advantageous. A particular advantage is that the dosages used in the herbicidal compositions and the effective dosages of herbicidal compounds can be adjusted to such a low level that their soil action is optimally low. This does not only allow them to be employed in sensitive crops in the first place, but groundwater contaminations are virtually avoided. The active compound combination according to the invention allows the required application rate of the active substances to be reduced considerably.

The abovementioned properties and advantages are necessary for weed control practice to keep agricultural crops free from undesired competing plants, and thus to ensure and/or increase yield levels from the qualitative and quantitative angle. These novel herbicidal compositions markedly exceed the technical state of the art with a view to the properties described.

While the herbicidal compositions have an outstanding herbicidal activity against monocotyledonous and dicotyledonous weeds, crop plants of economically important crops, for example *dicotyledonous* crops such as soya, cotton, oilseed rape, sugarbeet, or graminaceous crops such as wheat, barley, rye, oats, millet, rice or corn, are damaged only to a minor extent, if at all. This is why the present herbicidal compositions are highly suitable for the selective control of undesired plant growth in plantations of agricultural crops or of ornamentals.

In addition, the corresponding herbicidal compositions have outstanding growth-regulatory properties in crop plants. They engage in the plants' metabolism in a regulatory manner and can thus be employed for provoking direct effects on plant constituents and to facilitate harvesting such as, for example, by triggering desiccation and stunted growth. Moreover, they are also suitable for the general control and inhibition of undesired vegetative growth without simultaneously destroying the plants. Inhibition of vegetative growth is very important in a large number of *monocotyledonous* and *dicotyledonous* crops since lodging can thus be reduced, or prevented completely.

Owing to their herbicidal and plant-growth-regulatory properties, the herbicidal compositions can also be employed for controlling harmful plants in crops of genetically modified plants which are known or yet to be developed. As a rule, the recombinant plants are distinguished by specific advantageous characteristics, for example by resistances to certain pesticides, in particular certain herbicides, resistances to plant diseases or the causative organisms of plant diseases such as specific insects or microorganisms such as fungi, bacteria or viruses. Other specific characteristics relate, for example, to the harvested material with regard to quantity, quality, storability, composition and specific constituents. Thus, for example, transgenic plants are known whose starch content is increased, or whose starch quality is altered, or those where the harvested material has a different fatty acid composition.

The use of the herbicidal compositions in economically important transgenic crops of useful plants and ornamentals, for example of graminaceous crops such as wheat, barley, rye, oats, millet, rice and corn, or else crops of sugarbeet, cotton, soya, oilseed rape, potatoes, tomatoes, peas and other vegetables, is preferred. Preferably, the herbicidal compositions can be employed in crops of useful plants which resist the phytotoxic effects of the herbicides, or have been made to resist these effects by recombinant techniques.

When using the herbicidal compositions in transgenic crops, effects are frequently observed in addition to the effects against harmful plants to be observed in other crops, which are specific for the application in the transgenic crop in question, for example a modified or specifically widened weed spectrum which can be controlled, modified application rates which may be employed for application, preferably good combining ability with the further herbicidally acitve compounds to which the transgenic crop is resistant, and an effect on growth and yield level of the transgenic crop plants.

The present invention therefore also relates to a method for controlling undesired vegetation, preferably in crops of plants such as cereals (for example wheat, barley, rye, oats, rice, corn and millet), sugar beet, sugar cane, oilseed rape, cotton and soya, especially preferred in monocotyledonous plants such as cereals, for example wheat, barley, rye, oats, and their hybrids such as triticale, rice, corn and millet, wherein the herbicidal compositions according to the invention are applied to the harmful plants, plant parts, seeds of the plants or the area on which the plants grow, for example the area under cultivation.

The plant crops may also be genetically modified or have been obtained by mutation selection; they preferably tolerate acetolactate synthase (ALS) inhibitors.

The process for preparing the formulations according to the invention can be selected from a number of processes known per se which permit the preparation of solid formulations, such as water-dispersible powders (WP), granules (WG), and compacted products preparable therefrom, such as flakes, tablets, etc. From among these processes, preference is given to extrusion, pan and fluidized bed granulation, particularly preferably fluidized bed granulation. Common to all processes is that the individual components are combined in the respective ratios, as a result of the preparation.

The formulations according to the invention have excellent chemical stability during preparation and storage and are suitable in particular also for combinations of active compounds having different physicochemical properties. In addition, the formulations according to the invention have excellent physical stability, are easy to apply and easy to use and have high biological effectiveness and selectivity.

The pH for the formulations according to the invention, for example in 10% strength aqueous solution, is generally between 7 and 8.

Altogether, the formulations according to the invention have the desired long-term storage stability and can be applied without any problems.

EXAMPLES

The examples serve to illustrate the invention and do not limit the processes and compounds described therein.

Preparation Process 1:

The individual components in the respective ratios are dissolved or dispersed in water. The mixture formed is, using a fluidized-bed granulator, converted into water-soluble granules which, after granulation, have a predefined residual amount of water.

Preparation Process 2:

The individual components are mixed in the respective ratios. The mixture formed is, using an air jet mill, ground finely and then moistened with about 5% water. This moistened material is subjected to extrusion granulation using a dome extruder, for example a perforated dome having perforations of the width of 0.5-0.8 mm. The moist granules are then air-dried until their residual water content corresponds to the value defined beforehand.

In preparation process 2, for example, safeners are, as optional component (e), applied with the solvents (component e-1) and emulsifiers (component e-2) also to be used optionally to the carrier material (component e-3), and as a first process step, a flowable absorbate is prepared, which is then mixed with the other formulation components.

The examples shown in tables 1 and 2 were prepared using the preparation process 2 (residual water content: about 1% by weight).

DESCRIPTION OF THE PRODUCTS USED IN THE EXAMPLES:

| | |
|---|---|
| Propoxycarbazone-methyl sodium 95% | active compound (phenylsulfonylaminocarbonyltriazolinones), Bayer CropScience |
| Iodosulfuron-methyl sodium 91% | active compound (phenylsulfonylureas), Bayer CropScience |
| Amidosulfuron-methyl sodium 95% | active compound (other sulfonamides), Bayer CropScience |
| ® Kaolin Tec 1 | carrier material, low absorbency (kaolin, aluminum hydrosilicate), Ziegler & Co. |
| ® Harborlite 300 | carrier material, low absorbency (perlite), Lehmann & Voss |
| ® Texapon K12 | wetting agent of the alkyl sulfate type (Na lauryl sulfate), Cognis |
| ® Genapol X060-methyl | wetting agent of the nonionic alkylalkoxy type (tridecyl alcohol ethoxylate methyl ether), Clariant - substantially analogous to ® Lutensol ON 60 from WO-A-98/34482 |
| ® Hostapur OSB | wetting agent of the alkyl sulfonate type (Na alpha-olefinsulfonate), Clariant - analogous to ® Witconate 3202 from WO-A-98/34482 |
| ® Morwet EFW | wetting agent of the naphthalenesulfonic acid type (Na naphthalenesulfonate, alkylated), Akzo Nobel |
| ® Aerosol OTB | wetting agent of the sulfosuccinic acid derivative type (Na diisooctylsulfosuccinate), Cytec - analogous to ® Newkalgen EX-70 and ® Geropon SDS from EP-A-764404 |
| ® Morwet D425 | dispersing agent (condensate of naphthalenesulfonic acid and formaldehyde), Akzo Nobel |
| ® Luviskol K30 | binder (polyvinylpyrrolidone), BASF |
| ® Wacker ASP 15 | Antifoam agent, emulsifier, anionic (polydimethylsiloxane, absorbed on a solid carrier), Wacker |
| Mefenpyr-diethyl 94% | safener (dichlorophenylpyrazoline-3-carboxylic acid), Bayer CropScience |
| ® Solvesso 200ND | aromatic solvent (alkylated naphthalene), Exxon |
| ® Calsogen AR100 | emulsifier, anionic (Ca dodecylbenzenesulfonate), Clariant |
| ® Emulsogen 3510 | emulsifier, nonionic (alkylated EO/PO block copolymer), Clariant |
| ® Sipernat 50S | carrier material, high absorbency (precipitated silicic acid), Degussa |

TABLE 1

Examples 1-4 (prior art)

| Component | Name | 1 % by weight | 2 % by weight | 3 % by weight | 4 % by weight |
|---|---|---|---|---|---|
| (a) | Propoxycarbazone-methyl sodium 95% | 17.68 | 17.68 | 17.68 | 14.74 |
| (a) | Iodosulfuron-methyl sodium 91% | 1.10 | 1.10 | 1.10 | 0.91 |
| (a) | Amidosulfuron-methyl sodium 95% | — | — | — | 6.69 |
| (b) | ® Kaolin Tec 1 | 11.58 | 13.02 | 12.04 | 13.87 |
| (b) | ® Harborlite 300 | 5.00 | 5.00 | 5.00 | 5.00 |
| analogous to (c) | ® Texapon K12 | 12.00 | — | — | — |
| analogous to (c) | ® Genapol X060-methyl | | 6.00 | — | 6.00 |
| analogous to (c) | ® Hostapur OSB | — | — | 12.00 | — |
| (d) | ® Morwet D425 | 10.00 | 10.00 | 10.00 | 10.00 |
| (d) | ® Luviskol K30 | 5.00 | 5.00 | 5.00 | 2.00 |
| (d) | ® Wacker ASP 15 | 1.00 | 1.00 | 1.00 | 1.00 |
| (e) | Mefenpyr-diethyl 94% | 8.51 | 8.51 | 8.51 | 7.10 |
| (e-1) | ® Solvesso 200ND | 10.00 | 16.56 | 9.54 | 16.56 |
| (e-2) | ® Calsogen AR100 | 2.63 | 2.63 | 2.63 | 2.63 |
| (e-2) | ® Emulsogen 3510 | 1.50 | 1.50 | 1.50 | 1.50 |
| (e-3) | ® Sipernat 50S | 14.00 | 12.00 | 14.00 | 12.00 |

Note:
Table 1 shows solid water-dispersible standard formulations (granules, examples 1-4) which employ wetting agents (analogous to component c) from chemically different groups, such as ® Texapon K12 (Na lauryl sulfate), ® Genapol X060-methyl (tridecyl alcohol ethoxylate methyl ether) and ® Hostapur OSB (Na alpha-olefinsulfonate) which are very customary for formulating crop protection agents (prior art).

TABLE 2

Examples 5-8 (according to the invention)

| Component | Name | 5 % by weight | 6 % by weight | 7 % by weight | 8 % by weight |
|---|---|---|---|---|---|
| (a) | Propoxycarbazone-methyl sodium 95% | 17.68 | 17.68 | 14.74 | 14.74 |
| (a) | Iodosulfuron-methyl sodium 91% | 1.10 | 1.10 | 0.91 | 0.91 |
| (a) | Amidosulfuron-methyl sodium 95% | — | — | 6.69 | 6.69 |
| (b) | ® Harborlite 300 | 8.40 | 8.40 | — | — |
| (b) | ® Kaolin Tec 1 | 25.63 | 22.63 | 34.49 | 31.49 |
| (c) | ® Morwet EFW | 2.00 | — | 2.00 | — |
| (c) | ® Aerosol OTB | — | 5.00 | — | 5.00 |
| (d) | ® Morwet D425 | 15.00 | 15.00 | 15.00 | 15.00 |
| (d) | ® Luviskol K30 | 5.00 | 5.00 | 5.00 | 5.00 |
| (d) | ® Wacker ASP 15 | 1.00 | 1.00 | 1.00 | 1.00 |
| (e) | Mefenpyr-diethyl 94% | 8.51 | 8.51 | 7.10 | 7.10 |
| (e-1) | ® Solvesso 200ND | 8.37 | 8.37 | 7.00 | 7.00 |
| (e-2) | ® Calsogen AR100 | 0.53 | 0.53 | 0.44 | 0.44 |
| (e-2) | ® Emulsogen 3510 | 0.76 | 0.76 | 0.63 | 0.63 |
| (e-3) | ® Sipernat 50S | 6.02 | 6.02 | 5.00 | 5.00 |

Note:
Table 2 shows solid water-dispersible formulations according to the invention.

Table 3 summarizes the respective chemical stabilities of the formulations introduced in tables 1 (prior art) and 2 (according to the invention) in a comparative manner. In each case, the stability criterion used was the chemical degradation of the active sulfonamide compounds present after 2 weeks of storage at a temperature of 54° C. (method similar to the CIPAC MT 46 method).

TABLE 3

Stability of active compounds from the group of the sulfonamides

Degradation of active compounds from the group of the sulfonamides as a function of the wetting agent (component c)

| EX. NO. | Wetting agent | Propoxycarbazone-methyl sodium | | | Iodosulfuron-methyl sodium | | | Amidosulfuron-methyl sodium | | |
|---|---|---|---|---|---|---|---|---|---|---|
| | | Start % | 2 W 54° C. % | Degradation rel. % | Start % | 2 W 54° C. % | Degradation rel. % | Start % | 2 W 54° C. % | Degradation rel. % |
| 1 | ® Texapon K12 | 17.0 | 16.9 | 0.6 | 1.07 | 0.89 | 16.82 | — | — | — |
| 2 | ® Genapol X060-methyl | 18.0 | 17.7 | 1.7 | 1.04 | 0.9 | 13.46 | — | — | — |
| 3 | ® Hostapur OSB | 17.1 | 17 | 0.6 | 0.978 | 0.9 | 7.98 | — | — | — |
| 4 | ® Genapol X060-methyl | 14.3 | 14.2 | 0.7 | 0.638 | 0.5 | 21.63 | 6.36 | 5.5 | 13.5 |
| 5 | ® Morwet EFW | n.a. | n.a. | n.a. | n.a. | n.a. | n.a. | — | — | — |
| 6 | ® Aerosol OTB | n.a. | n.a. | n.a. | n.a. | n.a. | n.a. | — | — | — |
| 7 | ® Morwet EFW | 14.5 | 14.5 | 0 | 0.864 | 0.85 | 1.6 | 6.6 | 6.5 | 1.5 |
| 8 | ® Aerosol OTB | 14.5 | 14.5 | 0 | 0.856 | 0.856 | 0 | 6.59 | 6.52 | 1.1 |

Abbreviations:
n.a. = not available;
"EX. NO." = example number (for the compositions see tables 1 and 2);
"Start %" = active content in % by weight at the start of the storage test;
"2 W 54° C. %" = active compound content in % by weight after 2 weeks of storage at 54° C.;
"Degradation rel. %" = chemical degradation based on the active compound content at the start of the storage test (= 100%).

The data in table 3 clearly show that the use of the wetting agents according to the invention (examples 5-8) results in a stabilization of active compounds from the group of the sulfonamides in formulations, compared to the wetting agents of the prior art (examples 1-4).

The invention claimed is:

1. A solid water-dispersible formulation, comprising
   a component (a), comprising propoxycarbazone or a sodium salt thereof, amidosulfuron-methyl or a sodium salt thereof and iodosulfuron-methyl or a sodium salt thereof;
   a component (b), comprising one or more carrier materials selected from natural tectosilicates; and
   a component (c), comprising one or more wetting agents selected from salts of alkylated naphthalenesulfonic acids or salts of diisooctylsulfosuccinic acids.

2. The solid water-dispersible formulation as claimed in claim 1, wherein the component (b) comprises aluminum hydrosilicate.

3. The solid water-dispersible formulation as claimed in claim 1, wherein the wetting agent is a sodium salt of alkylated naphthalenesulfonic acid.

4. The solid water-dispersible formulation as claimed in claim 1, further comprising a component (d) selected from customary auxiliaries or additives.

5. The solid water-dispersible formulation as claimed in claim 4, wherein the component (d) is selected from the group consisting of a dispersing agent, a disintegrant, an antifoam agent, a tackifier, and a combination thereof.

6. The solid water-dispersible formulation as claimed in claim 1, further comprising a component (e), wherein component (e) is selected from one or more safeners.

7. The solid water-dispersible formulation as claimed in claim 6, wherein the one or more safeners are selected from the group consisting of mefenpyr-diethyl, isoxadifen-ethyl, 4-cyclopropylaminocarbonyl-N-(2-methoxybenzoyl)-benzene-sulfonamide, and 4-isopropylaminocarbonyl-N-(2-methoxy-benzoyDbenzene-sulfonamide.

8. The solid water-dispersible formulation as claimed in claim 6, wherein the component (e) optionally comprises solvents selected from aromatic hydrocarbons or aliphatic hydrocarbons.

9. The solid water-dispersible formulation as claimed in claim 6, wherein the component (e) optionally comprises emulsifiers selected from the salts of alkylated aromatic sulfonic acids, alkylated copolymers of ethylene oxide or alkylated copolymers of propylene oxide.

10. The solid water-dispersible formulation as claimed in claim 6, wherein the component (e) optionally comprises carrier materials selected from calcium silicates or precipitated silicic acids.

11. The solid water-dispersible formulation as claimed in claim 1, further comprising a component (f), wherein the component (f) is selected from one or more agrochemically active compounds different from the components (a) and (e).

12. A process for preparing a solid water-dispersible formulation as claimed in claim 1, comprising combining each component of claim 1 to form a mixture.

13. A method for controlling harmful plants, comprising applying an effective amount of a solid water-dispersible formulation as claimed in claim 1 to the harmful plants, to parts of the plants, to plant seeds, to an area on which the plants grow, or a combination thereof.

14. A process for preparing a herbicidal composition, comprising combining each component of the solid water-dispersible formulation as claimed in claim 1 to form a mixture.

15. A herbicidal composition, comprising a solid water-dispersible formulation as claimed in claim 1.

16. A method for controlling harmful plants, comprising applying an effective amount of a herbicidal composition as claimed in claim 15 to the harmful plants, to parts of the plants, to plant seeds, to the area on which the plants grow, or a combination thereof.

17. The solid water-dispersible formulation as claimed in claim 1, wherein the one or more natural tectosilicates is kaolin or aluminum hydrosilicate.

18. The solid water-dispersible formulation as claimed in claim 1, wherein the wetting agent is an alkylated naphthalenesulfonate.

* * * * *